US008238387B2

(12) United States Patent
Yamazoe

(10) Patent No.: US 8,238,387 B2
(45) Date of Patent: Aug. 7, 2012

(54) MODE-LOCKED LASER DEVICE, ULTRASHORT PULSE LIGHT SOURCE DEVICE, BROAD BANDWIDTH LIGHT SOURCE DEVICE, NON-LINEAR OPTICAL MICROSCOPY DEVICE, RECORDING DEVICE AND OPTICAL COHERENCE TOMOGRAPHY DEVICE

(75) Inventor: Shogo Yamazoe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 195 days.

(21) Appl. No.: 12/604,097

(22) Filed: Oct. 22, 2009

(65) Prior Publication Data
US 2010/0103961 A1 Apr. 29, 2010

(30) Foreign Application Priority Data
Oct. 27, 2008 (JP) ................. 2008-275756

(51) Int. Cl.
*H01S 3/098* (2006.01)
*H01S 3/08* (2006.01)
(52) U.S. Cl. .......... 372/18; 372/30; 372/92; 372/99
(58) Field of Classification Search .......... 372/18; 327/18, 92, 99
See application file for complete search history.

(56) References Cited

U.S. PATENT DOCUMENTS

| 7,106,764 | B1 * | 9/2006 | Weingarten et al. ............ 372/18 |
| 2006/0056468 | A1 | 3/2006 | Dantus et al. | |
| 2006/0142746 | A1 * | 6/2006 | Friedman et al. ............... 606/11 |
| 2007/0297464 | A1 * | 12/2007 | Adachi et al. ................... 372/18 |
| 2008/0317072 | A1 * | 12/2008 | Essaian et al. .................. 372/10 |
| 2008/0317073 | A1 * | 12/2008 | Adachi et al. ................... 372/18 |
| 2009/0021746 | A1 * | 1/2009 | Toida et al. ..................... 356/484 |
| 2009/0086771 | A1 * | 4/2009 | Usui et al. ........................ 372/18 |

FOREIGN PATENT DOCUMENTS

EP 2 042 893 A2 4/2009
JP 2002-536823 A 10/2002

OTHER PUBLICATIONS

EP Communication, dated Jan. 28, 2010, issued in corresponding EP Application No. 09013302.6, 13 pages.
Krainer et al., "77 GHz soliton modelocked Nd:YVO$_4$ laser," Electronics Letters, Oct. 26, 2000, vol. 36, No. 22, 2 pages, XP006015843.

(Continued)

*Primary Examiner* — Jessica Stultz
*Assistant Examiner* — Phillip Nguyen
(74) *Attorney, Agent, or Firm* — Sughrue Mion, PLLC

(57) ABSTRACT

There is provided a mode-locked laser device including: a resonator; a solid-state laser medium that is disposed in the resonator and outputs oscillation light in accordance with the incidence of excitation light; a saturable absorber that is disposed in the resonator and induces soliton mode-locking; a group velocity dispersion correction component that is disposed in the resonator and controls group velocity dispersion in the resonator; and an excitation portion that causes excitation light to be incident at the solid-state laser medium, wherein a resonator length of the resonator is at least a resonator length with which soliton mode-locking is inducible and is less than a resonator length with which non-soliton mode-locking is inducible.

19 Claims, 18 Drawing Sheets

OTHER PUBLICATIONS

Byun et al., "High-repetition-rate, 491 MHz, femtosecond fiber laser with low timing jitter," Optics Letters, Oct. 1, 2008, vol. 33, No. 19, pp. 2221-2223, XP-001517239.

Hönninger et al., "Q-switching stability limits of continuous-wave passive mode locking," J. Opt. Soc. Am. B., vol. 16, No. 1, Jan. 1999, pp. 46-56.

L. Krainer, et al., "Compact 10-GHz Nd:GdVO$_4$ laser with 0.5-W average output power and low timing jitter," Optics Letters, 2004, pp. 2629-2631, vol. 29, No. 22.

C. Honninger, et al, Q-switching stability limits of continuous-wave passive mode locking, J. Opt. Soc. Am. B., 1999, pp. 46-56, vol. 16, No. 1.

* cited by examiner

MODE-LOCKED LASER DEVICE, ULTRASHORT PULSE LIGHT SOURCE DEVICE, BROAD BANDWIDTH LIGHT SOURCE DEVICE, NON-LINEAR OPTICAL MICROSCOPY DEVICE, RECORDING DEVICE AND OPTICAL COHERENCE TOMOGRAPHY DEVICE

CROSS-REFERENCE TO RELATED APPLICATION

This application is based on and claims priority under 35 USC 119 from Japanese Patent Application No. 2008-275756 filed on Oct. 27, 2008, the disclosure of which is incorporated by reference herein.

BACKGROUND

1. Technical Field

The present invention relates to a mode-locked laser device, an ultrashort pulse light source device, a broad bandwidth light source device, a non-linear optical microscopy device, a recording device and an optical coherence tomography device, and particularly relates to a mode-locked laser device that outputs ultrashort pulse light and an ultrashort pulse light source device, broad bandwidth light source device, non-linear optical microscopy device, recording device and optical coherence tomography device.

2. Related Art

Ultrashort pulse light with pulse widths of picoseconds or femtoseconds is used in applications that utilize non-linear effects, such as secondary photon absorption induced by the very large peak powers, second harmonic generation (SHG), coherent anti-Stokes Raman scattering (CARS) and the like.

A technique for generating ultrashort pulse light is the "mode-locking" method, in which a solid-state laser medium disposed in a resonator is excited by a semiconductor laser or suchlike and the phases of numerous oscillating longitudinal modes are synchronized. A laser device that generates pulsed laser light with this method is referred to as a mode-locked laser device.

As mode-locked laser devices that are currently commercially available, TSUNAMI, manufactured by SPECTRA-PHYSICS, CHAMELEON, manufactured by COHERENT, and so forth are widely used. However, these mode-locked lasers are laser devices that are based on titanium-sapphire crystals and have complex resonator structures, as illustrated in FIG. 17.

Because these resonator structures are complex and green solid-state lasers are used for excitation of the titanium-sapphire crystals, numbers of components are large and the laser devices themselves are very expensive, being ten million yen or more. Moreover, in regard to output stability, feedback functions have to be added to optimize the resonator mirrors and make outputs constant in response to output variations, and these are unstable such that oscillation ceases after several weeks. Furthermore, the laser devices are large, being tabletop size.

In these mode-locked lasers, a mode-locking technique referred to as Kerr lens mode-locking is employed. However, with this technique, it is difficult for the mode-locking to self-start, and a driving mechanism for causing self-starting (corresponding to the AOM (acousto-optic modulator) in FIG. 17) must be provided. Moreover, in order to induce mode-locking, structuring for conditions in which the resonator destabilizes is necessary, and this is one of the causes of the aforementioned complexity of the resonator structure and of output destabilization.

In recent years however, mode-locked lasers that use a component known as a semiconductor saturable absorbed mirror (SESAM) have been reported. By using this component, it is possible to easily make mode-locking self-starting, and the mode-locking can be stably applied. Moreover, because this component functions as a resonator mirror, the resonator structure can be simplified, and a low-cost mode-locked laser with a compact and simple resonator structure can be realized.

FIG. 18 (see Optics Letters, vol. 29, pp. 2629-2631 (2004)) illustrates a mode-locked laser that uses a semiconductor saturable absorber mirror (SESAM hereinafter). As shown in FIG. 18, the resonator has a linear structure, the two ends of which are constituted by a concave mirror 200 and a SESAM 202. Only three components constitute the resonator—the concave mirror 200, the SESAM 202 and a solid-state laser medium 204—which is an extremely simple structure. Therefore, a lowering of costs and a reduction in size are possible. Furthermore, because the resonator length is short at a few cm, even if the resonator mirror and the like are displaced by environmental changes in temperature, humidity and the like, displacement of the resonator optical axis is suppressed, and a very high stability mode-locked laser can be realized. The resonator length of the commercially available mode-locked laser using titanium-sapphire that is illustrated in FIG. 17 is long, at around 2 m, which is another major factor in destabilization of output of the mode-locked laser, and the resonator length has a large effect on output stabilization.

Now, in order to start or maintain mode-locking in a mode-locked laser that uses a SESAM, a pulse energy $E_p$ inside the resonator must be maintained at least a mode-locking threshold energy $E_{c,p}$ expressed by equation (S1) (see J. Opt. Soc. Am. B, vol. 16, pp. 46-56 (1999)).

$$E_{c,p} = F_{sat,L} * F_{sat,S} * A_L * A_S * \Delta R \quad \text{(S1)}$$

Here, $F_{sat,L}$ is the saturation fluence of the laser medium, and is expressed as $h\nu/\sigma$, using the Planck constant h, an oscillation light frequency $\nu$ and a stimulated emission cross section $\sigma$ of the laser medium. $F_{sat,S}$ represents the saturation fluence of the SESAM, $A_L$ represents an oscillating light beam cross section in the laser medium, $A_S$ represents the oscillating light beam cross section at the SESAM, and $\Delta R$ represents the modulation depth of the SESAM.

The pulse energy $E_p$ in the resonator is expressed by the following equation, using an average output power $P_{out}$, an output mirror transmittance T and a repetition frequency of the pulse light $f_{rep}$.

$$E_p = (P_{out}/T)/f_{rep} \quad \text{(S2)}$$

The repetition frequency $f_{rep}$ is a number of round trips of the pulse light in the resonator in a unit of time, and is expressed by the following equation, using a resonator length L and the speed of light c.

$$f_{rep} = c/2L \quad \text{(S3)}$$

As is clear from the above equations (S2) and (S3), the shorter the resonator length, the smaller the pulse energy $E_p$ in the resonator. If the pulse energy $E_p$ in the resonator falls below the mode-locking threshold energy $E_{c,p}$ expressed by the preceding equation (S1), the mode-locking ceases to be in effect. Therefore, in order to shorten the resonator length given a constrained average output power $P_{out}$, it is necessary to reduce the mode-locking threshold energy as much as possible.

To reduce the mode-locking threshold energy, it is necessary to reduce the respective parameters in equation (S1). $F_{sat,S}$ and $\Delta R$ are characteristics of the SESAM. Minimum values of these in SESAMs that are currently commercially available are $F_{sat,S}$=70 μJ/cm², and $\Delta R$=0.4%, approximately. $A_L$ and $A_S$ are at least about $2.85 \times 10^{-5}$ cm². If the cross section were reduced further, the resonator would become unstable, and there would be a risk of destroying the SESAM. Therefore, to obtain a mode-locked laser with a shorter resonator length, an Nd-doped laser medium with which the stimulated emission cross section σ can be made larger and $F_{sat,L}$ can be made smaller is used (see, for example, Japanese National Publication No. 2002-536823).

However, with an Nd-doped laser medium, the stimulated emission cross section is large but the oscillation bandwidth is narrow. Therefore, even at the shortest, optical pulses shorter than several picoseconds cannot be generated. In recent years however, a Yb-doped laser medium that can be excited by a high-output infrared semiconductor laser has attracted interest as a laser medium for a high-output ultrashort pulse mode-locked laser. This laser medium has a wide oscillation bandwidth, and can generate optical pulses of hundreds of femtoseconds. A difference in pulse width between picoseconds and hundreds of femtoseconds is similar to values of peak power being an order of magnitude different. When considering, for example, secondary photon absorption, this order of magnitude difference means a difference of two orders of magnitude in absorption. Thus, this difference in pulse widths is significant for non-linear applications.

However, the Yb-doped semiconductor laser medium has a small stimulated emission cross section σ, and with a mode-locking threshold energy derived from the following equation (1), it is difficult to make the resonator length less than 15 cm.

$$\frac{c \times E_{c,p,s} \times T}{2 \times P_{out}} \leq L < \frac{c \times E_{c,p} \times T}{2 \times P_{out}} \tag{1}$$

In other words, it has been difficult to realize a small-size ultrashort pulse mode-locked laser with a pulse width of hundreds of femtoseconds and a resonator length of less than 15 cm. That is, it has been difficult to make the length of a resonator in a simple structure as illustrated in FIG. 18 shorter and to realize an ultrashort pulse (hundreds of femtoseconds) mode-locked laser that is compact and low in cost.

SUMMARY

The present invention has been made in order to solve the problem described above, and an object is to provide a compact, low-cost mode-locked laser device capable of outputting ultrashort pulse light, and an ultrashort pulse light source device, a broad bandwidth light source device, a non-linear optical microscopy device, a recording device and an optical coherence tomography device.

In order to solve the above-mentioned problem, a first aspect of the present invention provides a mode-locked laser device including:

a resonator;

a solid-state laser medium that is disposed in the resonator and outputs oscillation light in accordance with the incidence of excitation light;

a saturable absorber that is disposed in the resonator and induces soliton mode-locking;

a group velocity dispersion correction component that is disposed in the resonator and controls group velocity dispersion in the resonator; and an excitation portion that causes excitation light to be incident at the solid-state laser medium, wherein a resonator length of the resonator is at least a resonator length with which soliton mode-locking is inducible and is less than a resonator length with which non-soliton mode-locking is inducible.

According to this invention, the respective members are structured such that, in the mode-locked laser that is provided with the saturable absorber and the group velocity dispersion correction component and in which soliton mode-locking is inducible, the resonator length of the resonator is at least a resonator length with which soliton mode-locking may be induced but less than a resonator length with which non-soliton mode-locking may be induced. Therefore, the resonator length may be made shorter than in a mode-locked laser device with non-soliton mode-locking. Thus, a compact, low-cost mode-locked laser device capable of outputting ultrashort optical pulses is provided.

Specifically, a second aspect of the present invention provides the mode-locked laser device according to the first aspect, wherein the resonator length satisfies the following equation (1):

$$\frac{c \times E_{c,p,s} \times T}{2 \times P_{out}} \leq L < \frac{c \times E_{c,p} \times T}{2 \times P_{out}} \tag{1}$$

in which L is the resonator length, c is the speed of light, $E_{c,p,s}$ is a mode-locking threshold energy of soliton mode-locking, which is expressed in the following equation (2), T is transmissivity of an optical member at a side at which the oscillation light is outputted, Pout is a desired average output power of the oscillation light outputted from the solid-state laser medium, and $E_{c,p}$ is a mode-locking threshold energy of non-soliton mode-locking, which is expressed in the following equation (3):

$$E_{c,p,s} = \tag{2}$$

$$\frac{1}{3E_{sat,L}gK^2} + \frac{2^{1/3}}{3E_{sat,L}gK^2 \left( \frac{-2 + 27E_{sat,L}^2 g^2 K^4 E_{c,p}^2 +}{\sqrt{-4 + (-2 + 27E_{sat,L}^2 g^2 K^4 E_{c,p}^2)^2}} \right)^{1/3}} +$$

$$\frac{\left(-2 + 27E_{sat,L}^2 g^2 K^4 + E_{c,p}^2 + \sqrt{-4 + (-2 + 27E_{sat,L}^2 g^2 K^4 E_{c,p}^2)^2}\right)^{1/3}}{3 \times 2^{1/3} E_{sat,L} gK^2}$$

K being expressed by the following equation $$K = \frac{4\pi n_2 L_K}{D_2 A_L \lambda_o \Delta v_g} \cdot \frac{0.315}{1.76} \tag{3}$$

$$E_{c,p} = \sqrt{F_{sat,L} \times F_{sat,s} \times A_L \times A_S \times \Delta R}$$

in which $E_{sat,L}$ is expressed by $F_{sat,L} * A_L$, $F_{sat,L}$ is a saturation fluence of the solid-state laser medium, and $A_L$ is a beam diameter of the oscillation light in the solid-state laser medium, and g is a gain of the solid-state laser medium, $n_2$ is a non-linear refractive index of the solid-state laser medium, $L_K$ is a length of the solid-state laser medium, $D_2$ is a negative dispersion amount in the resonator, $\lambda_0$ is a central wavelength of the oscillation light, $\Delta v_g$ is a bandwidth of the oscillation light, $F_{sat,S}$ is a saturation fluence of the saturable absorber, $A_S$ is a beam diameter of the oscillation light in the saturable absorber, and $\Delta R$ is a modulation depth of the saturable absorber.

A third aspect of the present invention provides the mode-locked laser device according to the first aspect, wherein the resonator length is at most 150 mm.

A fourth aspect of the present invention provides the mode-locked laser device according to the third aspect, wherein the resonator length is at most 75 mm.

Further, a fifth aspect of the present invention provides the mode-locked laser device according to the first aspect, wherein a stimulated emission cross section of the solid-state laser medium is at least $1 \times 10^{-21}$ cm$^2$ and at most $5 \times 10^{-19}$ cm$^2$.

Further, a sixth aspect of the present invention provides the mode-locked laser device according to the fifth asect, wherein the solid-state laser medium comprises any of Yb:KGW (KGd(WO$_4$)$_2$), Yb:KYW (KY(WO$_4$)$_2$), Yb:YAG (Y$_3$Al$_5$O$_{12}$), Yb:Y$_2$O$_3$, Yb:Sc$_2$O$_3$, Yb:Lu$_2$O$_3$, Yb:GdCOB (Ca$_4$GdO(BO$_3$)$_3$), Yb:SYS (SrY$_4$(SiO$_4$)$_3$), Yb:BOYS (Sr$_3$Y(BO$_3$)$_3$), Yb:YVO$_4$, Yb:GdVO$_4$, Alexandrite (Cr:BeAl$_2$O$_4$), Cr:LiSAF (LiSrAlF$_6$), Cr:LiSGAF (LiSrGaF$_6$), Cr:LiCAF (LiCaAlF$_6$)), Cr:forsterite (Mg$_2$SiO$_4$), Cr:YAG (Y$_3$Al$_5$O$_{12}$), Cr:Ca$_2$GeO$_4$, Ti:Al$_2$O$_3$, Nd:Glass and Er:Yb:Glass.

Further, a seventh aspect of the present invention provides the mode-locked laser device according to the first aspect, wherein a negative dispersion amount in the resonator is at least $-3000$ fs$^2$ and at most 0 fs$^2$.

In addition, an eighth aspect of the present invention provides the mode-locked laser device according to the seventh aspect, wherein the negative dispersion amount in the resonator is at least $-1000$ fs$^2$ and at most 0 fs$^2$.

Further, a ninth aspect of the present invention provides the mode-locked laser device according to the second aspect, wherein the transmissivity of the optical member at the side at which the oscillation light is outputted is at least 0.1% and at most 5%.

In addition, a tenth aspect of the present invention provides the mode-locked laser device according to the ninth aspect, wherein the transmissivity is at least 0.1% and at most 3%.

Further, an eleventh aspect of the present invention provides the mode-locked laser device according to the second aspect, wherein the modulation depth of the saturable absorber is at least 0.5% and at most 5%, and the saturation fluence of the saturable absorber is at least 50 µJ/cm$^2$ and at most 200 µJ/cm$^2$.

Further, a twelfth aspect of the present invention provides the mode-locked laser device according to the second aspect, wherein the average output power is at least 0.1 mW and at most 10 W.

In addition, a thirteenth aspect of the present invention provides the mode-locked laser device according to the twelfth aspect, wherein the average output power is at least 0.1 mW and at most 5 W.

Further, a fourth aspect of the present invention provides the mode-locked laser device according to the first aspect, wherein the resonator is formed with a pair of resonator mirrors disposed on a straight line.

Further, a fifteenth aspect of the present invention provides the mode-locked laser device according to the first aspect, wherein the saturable absorber is a semiconductor saturable absorber mirror.

Further, a sixteenth aspect of the present invention provides a non-linear optical microscopy device including:
 a mode-locked laser device according to the first aspect;
 a first focusing optical system that focuses pulse light from the mode-locked laser device at a sample;
 a second focusing optical system that focuses fluorescence from the sample; and
 a detection section that detects the fluorescence focused by the second focusing optical system.

According to this invention, a small, low-cost non-linear optical microscopy device is provided.

A seventeenth aspect of the present invention provides an ultrashort pulse light source device including:
 a mode-locked laser device according to the first aspect;
 a non-linear crystal;
 a focusing lens that focuses pulse light from the mode-locked laser device at the non-linear crystal; and
 a filter that, of light transmitted through the non-linear crystal, cuts near-infrared light and transmits ultrashort pulse light in the visible wavelength region.

According to this invention, a small, low-cost ultrashort pulse light source device is provided.

An eighteenth aspect of the present invention provides a recording device including:
 an ultrashort pulse light source device according to claim 17; and
 a focusing optical system that focuses ultrashort pulse light from the ultrashort pulse light source device at a recording medium to serve as writing light.

According to this invention, a small, low-cost recording device is provided.

Further, a nineteenth aspect of the present invention provides a broad bandwidth light source device including:
 a mode-locked laser device according to the first aspect;
 a non-linear optical fiber; and
 a focusing lens that focuses pulse light from the mode-locked laser device at the non-linear fiber.

According to this invention, a small, low-cost broad bandwidth light source device is provided.

Further, a twentieth aspect of the present invention provides an optical coherence tomography device including:
 a broad bandwidth light source device according to the nineteenth aspect;
 a reflection portion that reflects light from the broad bandwidth light source device in a predetermined direction;
 a focusing optical system that focuses other light from the broad bandwidth light source device at a sample;
 a movement section that relatively moves the light focused by the focusing optical system and the sample; and
 a detection section that detects interference light between the light reflected by the reflection portion and light returned from the sample.

According to this invention, a small, low-cost optical coherence tomography device is provided.

According to the present invention, there is an effect in that a compact, low-cost mode-locked laser device capable of outputting ultrashort pulse light, an ultrashort pulse light source device, a broad bandwidth light source device, a non-linear optical microscopy device, a recording device and an optical coherence tomography device may be provided.

BRIEF DESCRIPTION OF THE DRAWINGS

Exemplary embodiments of the present invention will be described in detail based on the following figures, wherein.

DETAILED DESCRIPTION

Herebelow, exemplary embodiments of the present invention will be described with reference to the drawings.

First Exemplary Embodiment

As described earlier, a solid-state laser medium doped with Yb has a small stimulated emission cross section σ and, with the mode-locking threshold energy derived from the aforementioned equation (S1), it has been difficult to realize a small-size ultrashort pulse mode-locked laser with a pulse width at hundreds of femtoseconds and a resonator length of 15 cm or less.

Therefore, in the present exemplary embodiment, a mode-locked laser device is described that, by using the mode-locking technique known as soliton mode-locking, may lower the mode-locking threshold energy and realize ultrashort optical pulses of several hundred fs with a structure that is simple and has a short resonator length.

Figure 17:
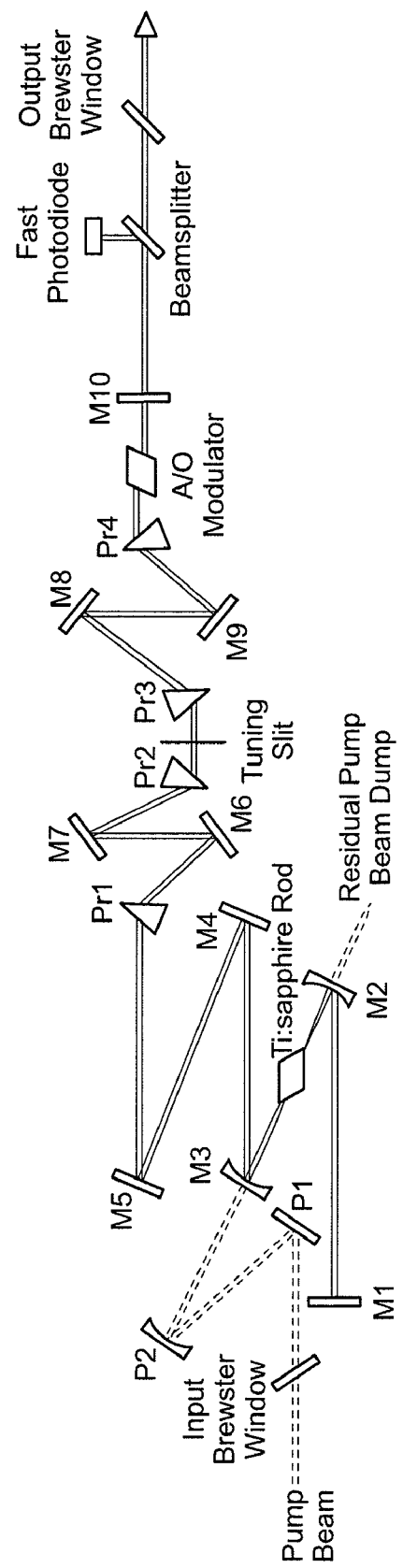
FIG. 17 is a structural diagram of a mode-locked laser device relating to a prior art example.
Figure 18:
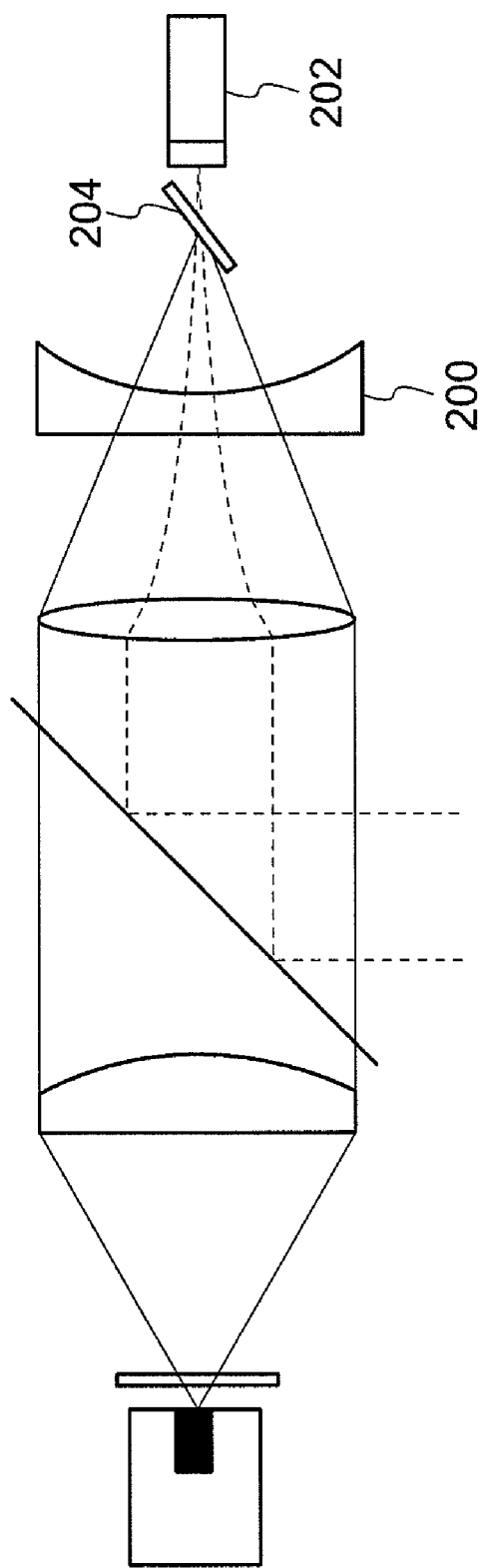
FIG. 18 is a structural diagram of a mode-locked laser device relating to a prior art example.

Usually, in order to generate ultrashort optical pulses of hundreds of fs, a group velocity dispersion correction component is disposed in the resonator for controlling group velocity dispersion within the resonator. In the mode-locked laser device illustrated in the earlier mentioned FIG. 17, four prisms Pr1 to Pr4 correspond to a group velocity dispersion correction component. When using a semiconductor saturable absorber mirror too, group velocity dispersion is similarly corrected using prisms or the like and, by inducing the soliton mode, ultrashort optical pulses of hundreds of fs may be provided.

According to Optics Letters, vol. 29, pp. 2629-2631 (2004), in a state in which this soliton mode-locking is induced, the mode-locking threshold energy is expressed by equation (2).

$$E_{c,p,s} = \frac{1}{3E_{sat,L}gK^2} + \frac{2^{1/3}}{3E_{sat,L}gK^2 \left( \frac{-2 + 27E_{sat,L}^2 g^2 K^4 E_{c,p}^2 +}{\sqrt{-4 + (-2 + 27E_{sat,L}^2 g^2 K^4 E_{c,p}^2)^2}} \right)^{1/3}} + \frac{\left(-2 + 27E_{sat,L}^2 g^2 K^4 + E_{c,p}^2 + \sqrt{-4 + (-2 + 27E_{sat,L}^2 g^2 K^4 E_{c,p}^2)^2}\right)^{1/3}}{3 \times 2^{1/3} E_{sat,L} gK^2} \quad (2)$$

K being expressed by the following equation $$K = \frac{4\pi n_2 L_K}{D_2 A_L \lambda_o \Delta v_g} \cdot \frac{0.315}{1.76} \quad (3)$$

$$E_{c,p} = \sqrt{F_{sat,L} \times F_{sat,s} \times A_L \times A_S \times \Delta R}$$

The mode-locking threshold energy in equation (2) is smaller than the mode-locking threshold energy in a case of non-soliton mode-locking as in the earlier mentioned equation (S1). That is, by forming a structure that induces soliton mode-locking, the mode-locking threshold energy may be lowered, the resonator length may be shortened correspondingly, and a compact, high-stability, low-cost ultrashort pulse mode-locked laser may be realized.

Figure 2:
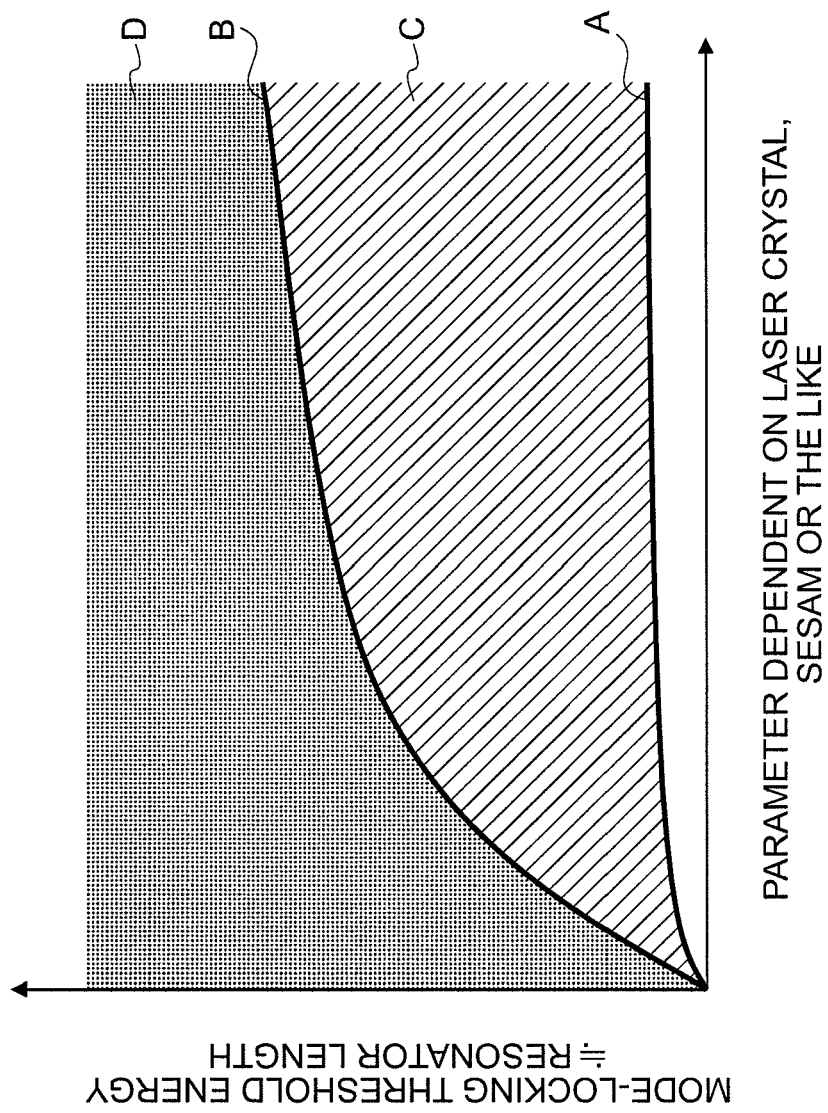
FIG. 2 is a graph illustrating a relationship between various parameters of a solid-state laser medium, a SESAM and the like and a mode threshold energy.

FIG. 2 shows a graph of mode threshold energies (≈resonator lengths) established in accordance with various parameters of the solid-state laser medium, SESAM and the like. The mode threshold energy for soliton mode-locking, expressed by the above expression (2), varies as shown by the mode threshold energy curve A in accordance with the various parameters of the solid-state laser medium, SESAM and the like. The mode threshold energy for non-soliton mode-locking, expressed by the above expression (3), varies as shown by the mode threshold energy curve B in accordance with the various parameters of the solid-state laser medium, SESAM and the like.

As described above, when a mode threshold energy is lower, the resonator length may be shortened correspondingly. As shown in FIG. 2, the mode threshold energy of soliton mode-locking is significantly smaller than the mode threshold energy of non-soliton mode-locking Accordingly, in the mode-locked laser device relating to the present exemplary embodiment, the various parameters of the mode-locked laser device are specified such that a pulse energy inside the resonator is within the scope of a region C at or above the soliton mode-locking mode threshold energy curve A and below the non-soliton mode-locking mode threshold energy curve B. In a prior art mode-locked laser, because the mode-locked laser must be set such that the pulse energy in the resonator is within the scope of a region D at and above the mode threshold energy curve B, the resonator length cannot be shortened correspondingly, whereas in the mode-locked laser device relating to the present exemplary embodiment, because the various parameters of the mode-locked laser device are specified such that the pulse energy in the resonator is within the scope of region C, the resonator length may be shortened.

Below, specific structure of the mode-locked laser device relating to the present exemplary embodiment will be described.

Figure 1:
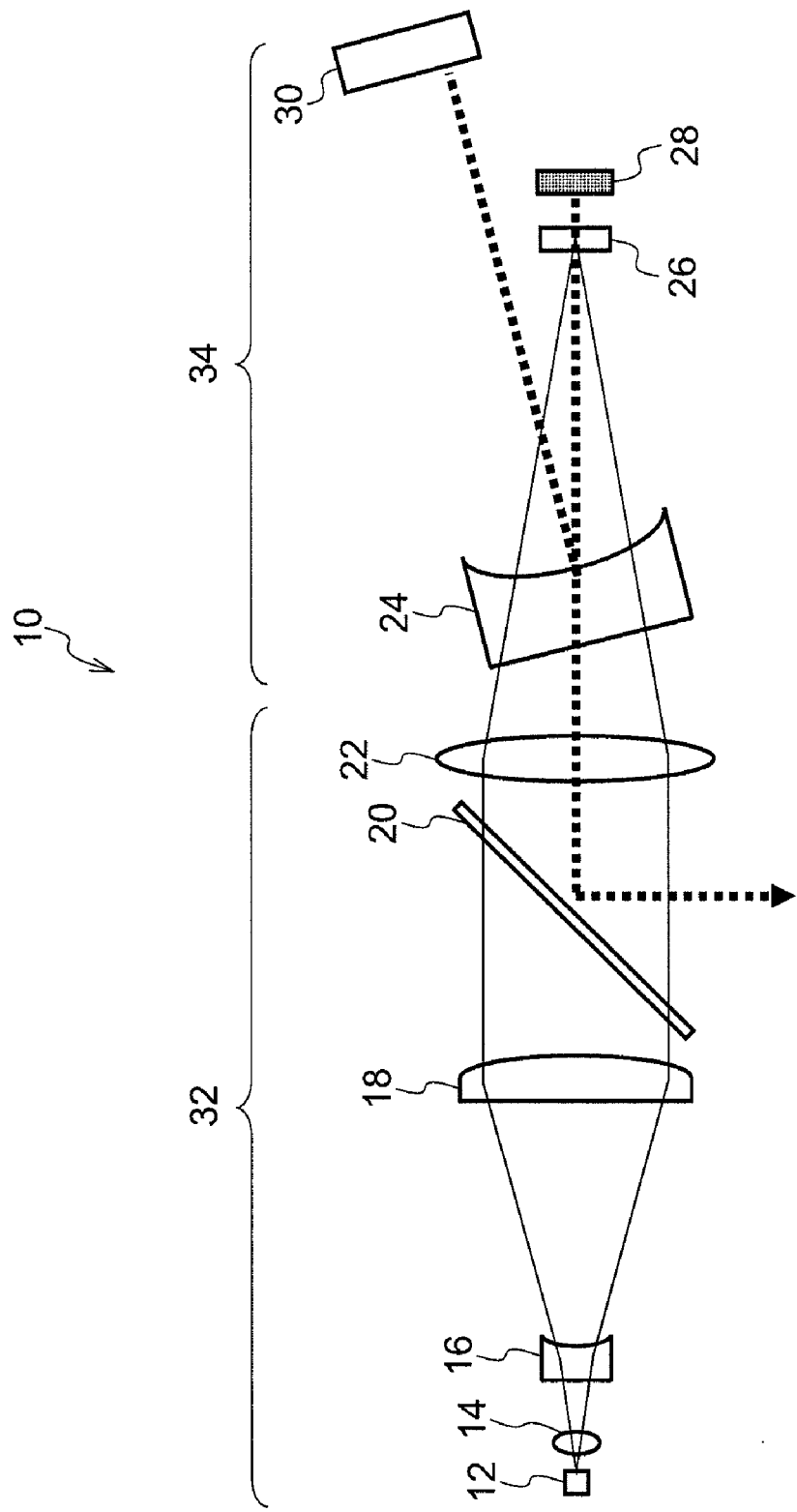
FIG. 1 is a schematic structural diagram of a mode-locked laser device relating to a first exemplary embodiment.

In FIG. 1, schematic structure of a mode-locked laser device 10 relating to the present exemplary embodiment is illustrated. As shown in FIG. 1, the mode-locked laser device 10 is structured to include a semiconductor laser 12, an aspherical lens 14, cylindrical lenses 16 and 18, a dichroic mirror 20, a focusing lens 22, a resonator mirror 24, a solid-state laser medium 26, a SESAM 28 and a negative dispersion mirror 30.

Here, an excitation optical system 32 is constituted by the semiconductor laser 12, the aspherical lens 14, the cylindrical lenses 16 and 18, the dichroic mirror 20 and the focusing lens 22.

A resonator 34 is constituted by the resonator mirror 24, the SESAM 28 and the negative dispersion mirror 30, and the solid-state laser medium 26 is disposed inside this resonator 34. Here, the resonator length of the resonator 34 is specified so as to satisfy the aforementioned equation (1).

For the semiconductor laser 12, for example, a semiconductor laser with a wavelength of 980 nm, an emission width of 50 μm and a maximum output power of 2.5 W, manufactured by OPTOENERGY, may be employed.

Excitation light emitted from the semiconductor laser 12 is collimated by the aspherical lens 14 and the cylindrical lenses 16 and 18.

The collimated excitation light is transmitted through the dichroic mirror 20 and focused at the solid-state laser medium 26 by the focusing lens 22, with a focusing distance of, for example, 40 mm. The solid-state laser medium 26 is formed of, for example, Yb:KYW.

An excitation beam spot with, for example, diameter 82 μm×34 μm may be formed in the solid-state laser medium 26 by the excitation optical system 32 with this structure. The solid-state laser medium 26 is excited by the excitation light being focused from the excitation optical system 32.

At the dichroic mirror 20, which is disposed inside the excitation optical system 32, one face is subjected to, for example, an anti-reflection coating with a reflectivity of 2% or less for light of wavelengths of 980±5 nm and the other face is subjected to a dichroic coating with a reflectivity of 5% or less for light with wavelengths of 980±5 nm and a reflectivity of 98% or more for light with wavelengths of 1045±10 nm.

At the resonator mirror 24, one face is a flat surface and the other face is, for example, a concave surface with a radius of curvature of 50 mm. The flat surface side is subjected to, for example, an anti-reflection coating with reflectivities of 2% or less for lights with wavelengths of 980±5 nm and 1045±10 nm, and the concave surface side is subjected to, for example, a dichroic coating with a reflectivity of 5% or less for light with wavelengths of 980±5 nm and a reflectivity of 99.3% for light with wavelengths of 1045±10 nm.

The resonator mirror 24 functions as an output mirror of the resonator 34, and a transmissivity thereof is preferably 5% or less in order to raise power within the resonator. In the structure with excitation by the simple semiconductor laser 12 and the short resonator length, in order to induce mode-locking the transmissivity is preferably set to 3% or less. Further, in a structure that is to provide pulse light of tens of Watts, which is required for non-linear optical applications, the transmissivity is preferably at least 0.1%.

The solid-state laser medium 26 may be formed of Yb:KYW using, for example, Yb:KYW with a doping density of Yb of 5% and a thickness of 1.5 mm. The two end faces of the solid-state laser medium 26 may be subjected to, for example, an anti-reflection coating with a reflectivity of 0.2% or less for light with wavelengths of 1045±10 nm.

In order to obtain pulse light with pulse widths of hundreds of fs, a wavelength bandwidth of at least 1 nm is necessary. A stimulated emission cross section of the solid-state laser medium 26 for such a bandwidth is preferably not more than $5\times10^{-19}$ cm$^2$. Meanwhile, in order to obtain a pulse energy exceeding the mode-locking threshold energy, that is, to obtain an adequate oscillation effect, the stimulated emission cross section of the solid-state laser medium 26 is preferably not less than $1\times10^{-21}$ cm$^2$.

For the SESAM 28, for example, a SESAM with a modulation depth (ΔR) of 0.5% for light with wavelengths of 1040 nm and a saturation fluence ($F_{sat,S}$) of 90 μJ/cm$^2$, manufactured by BATOP GmbH, may be used.

Now, in order to excite soliton mode-locking, the modulation depth of the SESAM 28 must be at least 0.5% and the saturation fluence at most 200 μJ/cm$^2$. Meanwhile, in order to avoid breakage of the SESAM 28, the modulation depth must be not more than 5% and the saturation fluence not less than 50 μJ/cm$^2$.

The negative dispersion mirror 30 is a mirror for correcting group velocity dispersion in the resonator. For example, a mirror manufactured by LAYERTECH may be used, with a dispersion amount of −1270 fs$^2$. At the solid-state laser medium 26, a dispersion amount required for obtaining pulse light of several hundred fs or less is 0 to −3000 fs$^2$, and a dispersion amount required for obtaining a pulse width of 100 fs or less is 0 to −1000 fs$^2$.

The resonator in the mode-locked laser device 10 has a V-form structure, that is, a structure in which the SESAM 28, the resonator mirror 24 and the negative dispersion mirror 30 are disposed so as to form a 'V' shape.

Light that passes through the focusing lens 22 is focused at the solid-state laser medium 26 and the SESAM 28 by the resonator mirror 24. Light reflected from the SESAM 28 passes through the solid-state laser medium 26 again, and is made parallel and deflected toward the negative dispersion mirror 30 by the resonator mirror 24.

A distance from the concave surface side of the resonator mirror 24 to the negative dispersion mirror 30 is, for example, 60 mm, and a distance from the concave surface side of the resonator mirror 24 to an end face of the SESAM 28 is, for example, 25 mm. With this resonator structure, an oscillation beam spot with diameter 60 μm may be formed on end faces of the solid-state laser medium 26 and the SESAM 28.

The mode-locked laser, due to the smaller size and the reduction in the number of components, may have lower costs. In addition, output variations due to positional changes of the resonator length, the resonator mirrors and the like may be kept to a minimum, and high stability may be realized. Therefore, stability may be raised by making the resonator length 150 mm or less and, preferably, stability may be further raised by making the resonator length 75 mm or less.

When an oscillation beam spot diameter on the solid-state laser medium 26 and the SESAM 28 is made smaller, the mode-locking threshold value falls, and it is easier to apply mode-locking. However, if the spot diameter is excessively small, problems arise such as light density becoming high and breakage of the SESAM 28 resulting, variations in output in response to mechanical variations caused by changes in the environment of the optical components that constitute the resonator becoming larger, and the like. Therefore, it is preferable to make the oscillation beam spot diameter at least a diameter of 30 μm. Meanwhile, if the spot diameter is excessively large, the mode-locking threshold value rapidly increases and mode-locking becomes difficult to apply. Therefore, the spot diameter is preferably not more than a diameter of 200 μm.

Light emitted from the resonator mirror 24 of the resonator 34 passes through the focusing lens 22, is reflected in the direction of the arrow in FIG. 1 by the dichroic mirror 20, and is outputted to the exterior as ultrashort pulse light.

Figure 3:
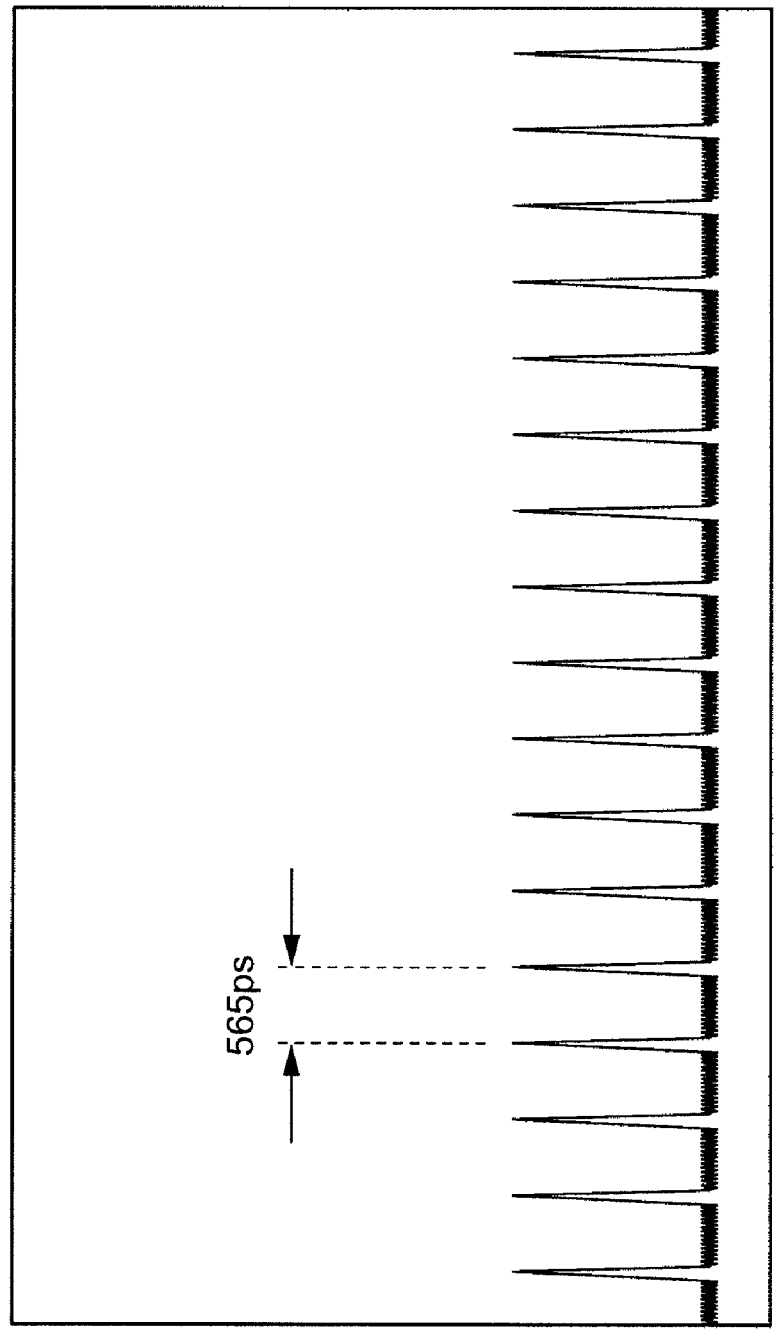
FIG. 3 is a waveform diagram showing an example of a pulse train time waveform.
Figure 4:
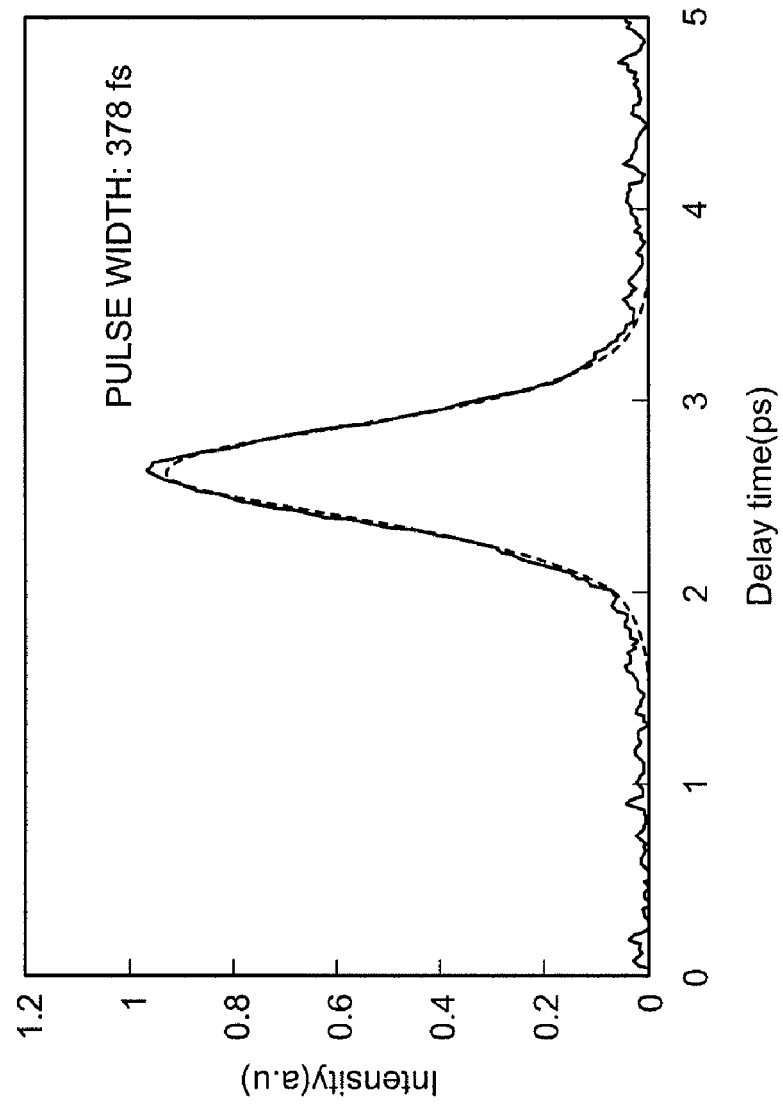
FIG. 4 is a waveform diagram showing a single pulse waveform.

FIG. 3 illustrates a waveform in which a waveform of pulse light emitted from the mode-locked laser device 10 is measured with a sampling oscilloscope, manufactured by AGILENT. FIG. 4 illustrates a single pulse waveform in which pulse light emitted from the mode-locked laser device 10 is measured with an autocollimator. As shown in FIG. 3, it is seen that a repetition interval of the pulses is 565 ps, which substantially matches the overall resonator length, and as shown in FIG. 4, it is seen that the pulse width is 378 fs, achieving the femtosecond class.

The average output power of the pulse light emitted from the resonator mirror 24 in this case is 63 mW for an excitation output power of 2200 mW, and the pulse energy in the resonator 34 is 5 nJ. If the aforementioned equation (S1) was applied to the mode-locked laser device 10, the mode-locking threshold energy would be 47 nJ, and mode-locking would not take effect unless the resonator length was extended by about 10 times, that is, to around 850 mm.

However, because the soliton mode-locking is induced by the negative dispersion mirror 30 and the mode-locking threshold energy is lowered, shortening of the resonator to tens of mm is possible even with the excitation output power of a single semiconductor laser, and a small-scale, simple-structure, low-cost ultrashort pulse mode-locked laser may be constituted.

Now, if the average output power of the pulse light outputted from the resonator mirror 24 exceeds 10 W, mode-locking other than soliton mode-locking may be induced. Meanwhile, for non-linear optical applications, peak powers of tens of Watts are required, and the average output power of the pulse light outputted from the resonator mirror 24 needs to be at least 0.1 mW. Therefore, the average output power of the pulse light outputted from the resonator mirror 24 needs to be at least 0.1 mW but not more than 10 W. Note that the maximum oscillation output power when using the maximum excitation output power provided by a contemporary single semiconductor laser is around 5 W, and that an average output power required to obtain a peak power of 1 kW, which is capable of inducing non-linear effects in biological materials and suchlike, is at least 10 mW.

Anyway, in the present exemplary embodiment, a case of using a laser crystal doped with Yb for the solid-state laser medium 26 has been described, but the solid-state laser medium is not limited thus. Solid-state laser mediums doped with $Cr^{3+}$ may be used (Alexandrite (Cr:Be $Al_2O_4$), Cr:LiSAF ($LiSrAlF_6$), Cr:LiSGAF ($LiSrGaF_6$) and Cr:LiCAF ($LiCaAlF_6$)). When using these solid-state laser mediums, ultrashort pulse lights with wavelengths of 700 to 1000 nm may be obtained.

Further, solid-state laser mediums doped with $Cr^{4+}$ may be used (Cr:forsterite ($Mg_2SiO_4$), Cr:YAG ($Y_3Al_5O_{12}$) and $Cr:Ca_2GeO_4$). When using these solid-state laser mediums, ultrashort pulse lights with wavelengths of 1200 to 1550 nm may be obtained.

As further alternatives as solid-state laser mediums, the following may be used: Yb:KGW ($KGd(WO_4)_2$), Yb:KYW ($KY(WO_4)_2$), Yb:YAG ($Y_3Al_5O_{12}$), Yb: $Y_2O_3$, $Yb:Sc_2O_3$, Yb: $Lu_2O_3$, Yb:GdCOB ($Ca_4GdO(BO_3)_3$), Yb:SYS ($SrY_4(SiO_4)_3$), Yb:BOYS ($Sr_3Y(BO_3)_3$), $Yb:YVO_4$, $Yb:GdVO_4$, Alexandrite (Cr: $BeAl_2O_4$), Ti: $Al_2O_3$, Nd:Glass, Er:Yb: Glass, and so forth.

Second Exemplary Embodiment

Next, a second exemplary embodiment of the present invention will be described. In the present exemplary embodiment, a mode-locked laser device with a structure in which a pair of resonator mirrors structuring a resonator are disposed on a straight line will be described.

Figure 5:
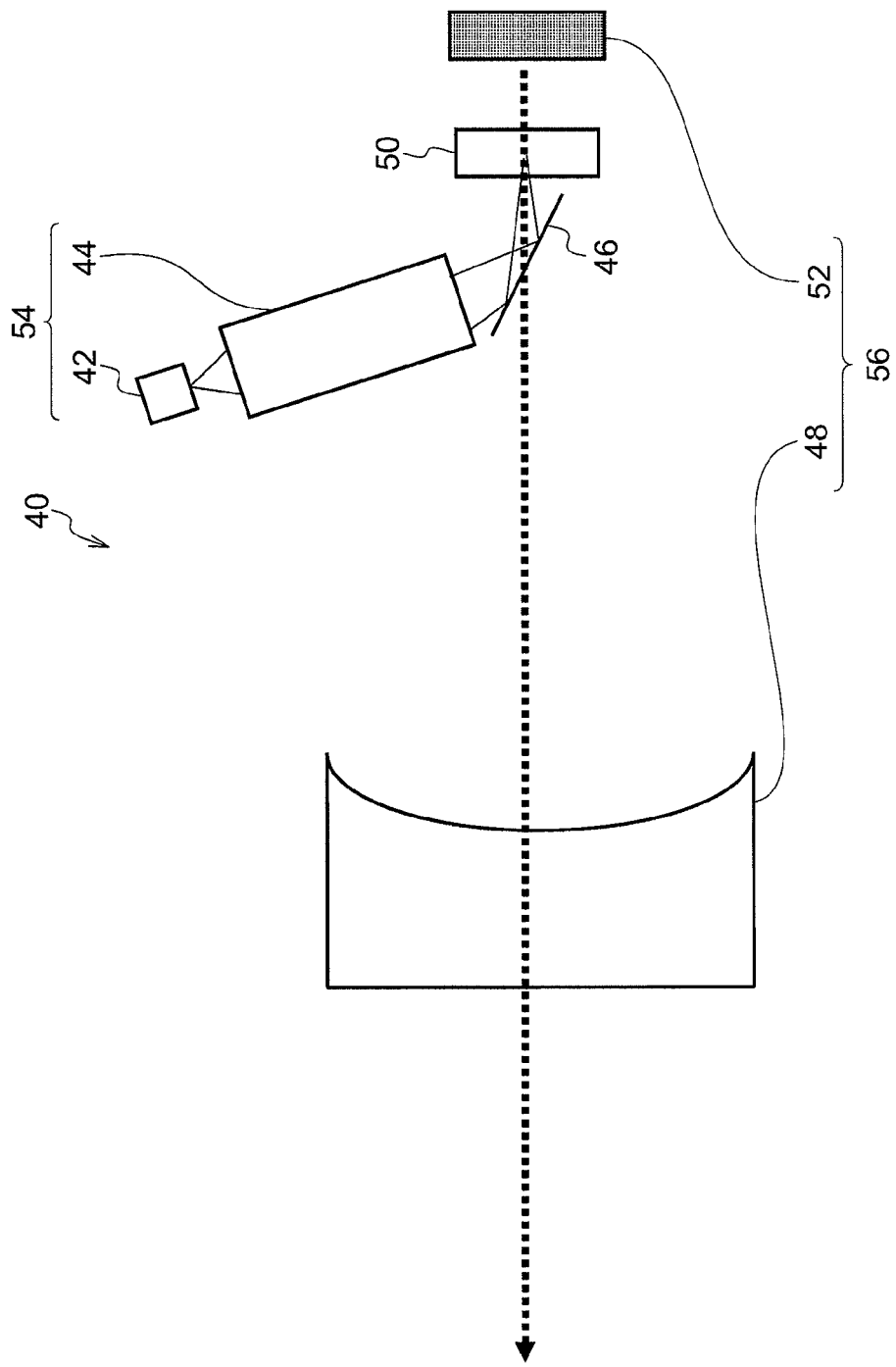
FIG. 5 is a schematic structural diagram of a mode-locked laser device relating to a second exemplary embodiment.

In FIG. 5, schematic structure of a mode-locked laser device 40 relating to the second exemplary embodiment is illustrated. As shown in FIG. 5, the mode-locked laser device 40 is structured to include a semiconductor laser 42, a SELFOC lens 44, a dichroic mirror 46, a negative dispersion mirror 48, a solid-state laser medium 50 and a SESAM 52.

Here, an excitation optical system 54 is constituted by the semiconductor laser 42 and the SELFOC lens 44.

A resonator 56 is constituted by the negative dispersion mirror 48 and the SESAM 52, which are disposed on a straight line, and the dichroic mirror 46 and the solid-state laser medium 50 are disposed inside this resonator 56. Herein, the resonator length of the resonator 56 is specified so as to satisfy the aforementioned equation (1).

The semiconductor laser 42 is similar to the semiconductor laser 12 of the mode-locked laser device 10 illustrated in FIG. 1.

The SELFOC lens 44 is subjected to, for example, an anti-reflection coating with a reflectivity of 2% or less for light with wavelengths of 980±5 nm, manufactured by Asahi Glass Co., Ltd.

The excitation light emitted from the semiconductor laser 42 is focused by the SELFOC lens 44, and is reflected in the direction of the solid-state laser medium 50 by the dichroic mirror 46.

The negative dispersion mirror 48 functions to correct group velocity dispersion in the resonator 56, similarly to the negative dispersion mirror 30 of the mode-locked laser device 10 illustrated in FIG. 1, and is an output mirror with a certain level of transmissivity for the oscillation light.

One face of the negative dispersion mirror 48 is a concave surface and has a radius of, for example, 50 mm. The concave surface side is subjected to a high-reflectivity negative dispersion coating with a transmissivity of 1% for light with wavelengths of 1045±10 nm and a group velocity dispersion amount of $-1000$ $fs^2$.

The other face of the negative dispersion mirror 48 is a flat surface, and is subjected to an anti-reflection coating with a reflectivity of 0.2% or less for light with wavelengths of 1045±10 nm.

For the SESAM 52, for example, a SESAM with a modulation depth ($\Delta R$) of 0.5% and a saturation fluence ($F_{sat,S}$) of 120 $\mu J/cm^2$, manufactured by BATOP GmbH, may be used. The SESAM 52 is disposed at, for example, a position substantially 50 mm from, for example, the flat surface side of the negative dispersion mirror 48, which functions as an output mirror.

The solid-state laser medium 50 is formed of, for example, Yb:KYW, and is similar to the solid-state laser medium 26 of the mode-locked laser device 10 illustrated in FIG. 1.

The dichroic mirror 46 is subjected to, for example, a dichroic coating with a reflectivity of 95% or more for light with wavelengths of 980±5 nm and a reflectivity of 0.2% or less for light with wavelengths of 1045±10 nm.

Figure 6:
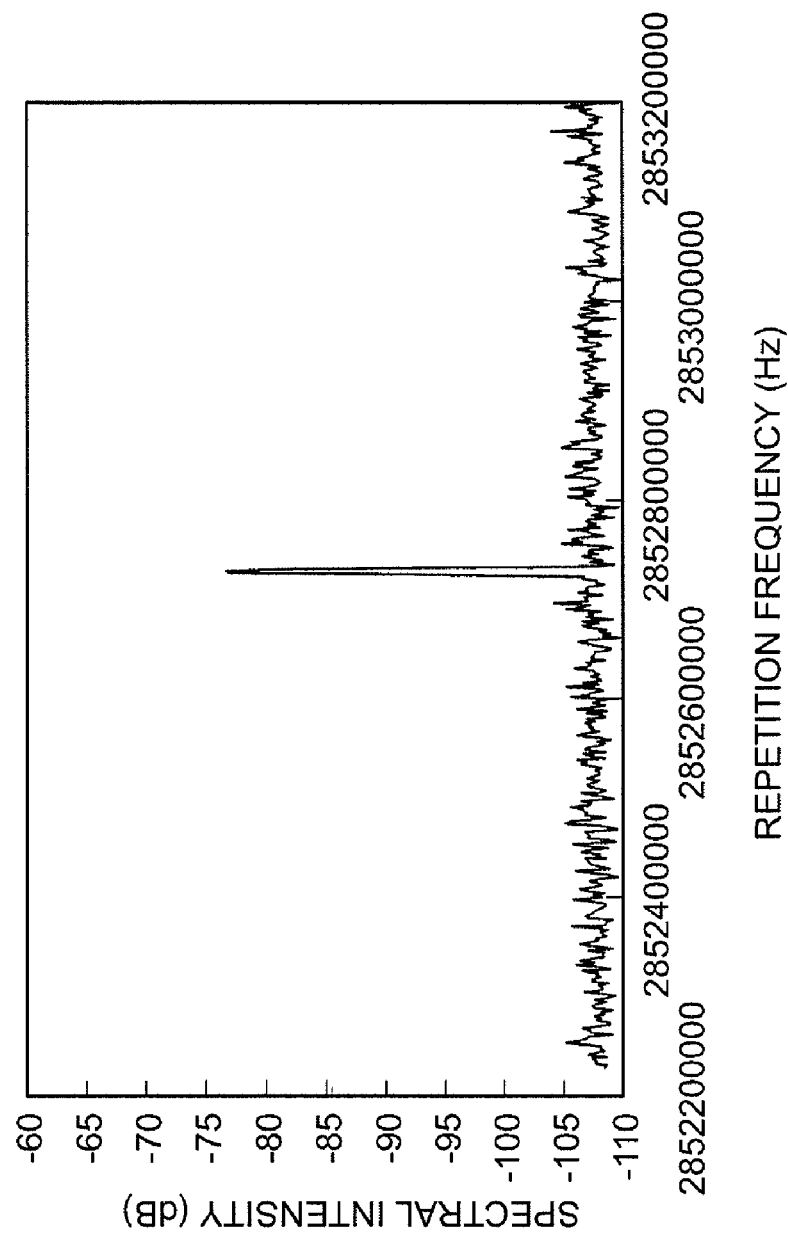
FIG. 6 is a graph illustrating a relationship between pulse repetition frequency and spectral intensity.

FIG. 6 is a graph illustrating a relationship between the pulse repetition frequency of pulse light emitted from the mode-locked laser device 40, measured with an RF spectral analyzer, and spectral intensity.

Figure 7:
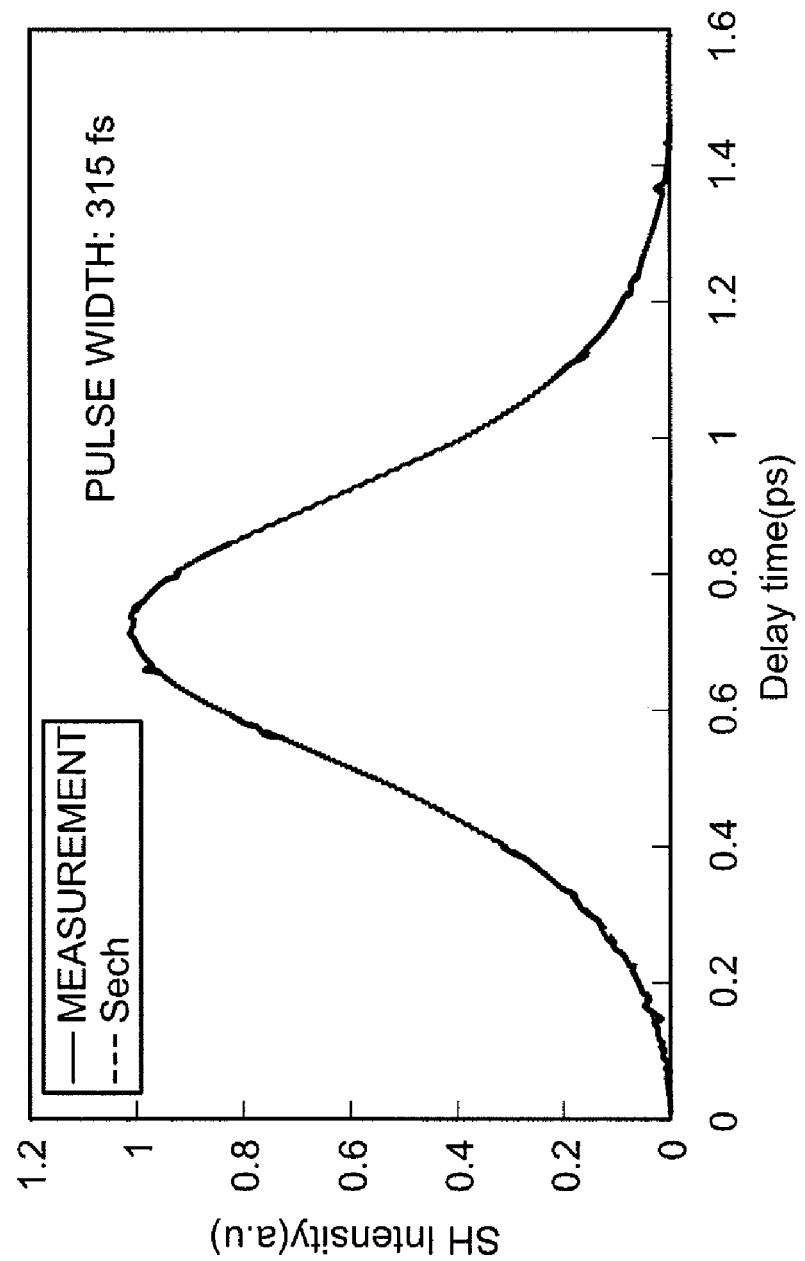
FIG. 7 is a diagram showing an example of a pulse waveform.

In FIG. 7, a result of measuring a pulse waveform in this case with an autocollimator is illustrated. As shown in FIG. 6, the repetition frequency of the pulses is 2.85 GHz, which substantially coincides with the mechanical resonator length of 50 mm (which is the length from the SESAM 52 to the flat surface side of the negative dispersion mirror 48, not taking account of the refractive index of the crystal). Even with such a short resonator length, ultrashort pulse light with a pulse width of 315 fs may be obtained. Further, output power in this case is 460 mW for an excitation light output power of 2350 mW, the pulse energy inside the resonator 56 is 16 nJ, and the mode-locking threshold pulse energy in non-soliton mode-locking according to the aforementioned equation (S1) would be 55 nJ. That is, by forming a structure to induce soliton mode-locking as in the mode-locked laser device 40 relating to the present exemplary embodiment, even though the pulse energy inside the resonator 56 is lower than the mode-locking threshold pulse energy of non-soliton mode-locking, mode-locking may be induced. Consequently, the resonator length may be shortened. Therefore, the resonator length may be further shortened compared to the mode-locked laser device 10 illustrated in FIG. 1, and a low-cost ultrashort pulse mode-locked laser at palmtop size may be realized.

Third Exemplary Embodiment

Next, a third exemplary embodiment of the present invention will be described. In the third exemplary embodiment, a non-linear optical microscopy device that uses the mode-locked laser device 40 described in the second exemplary embodiment will be described.

Figure 8:
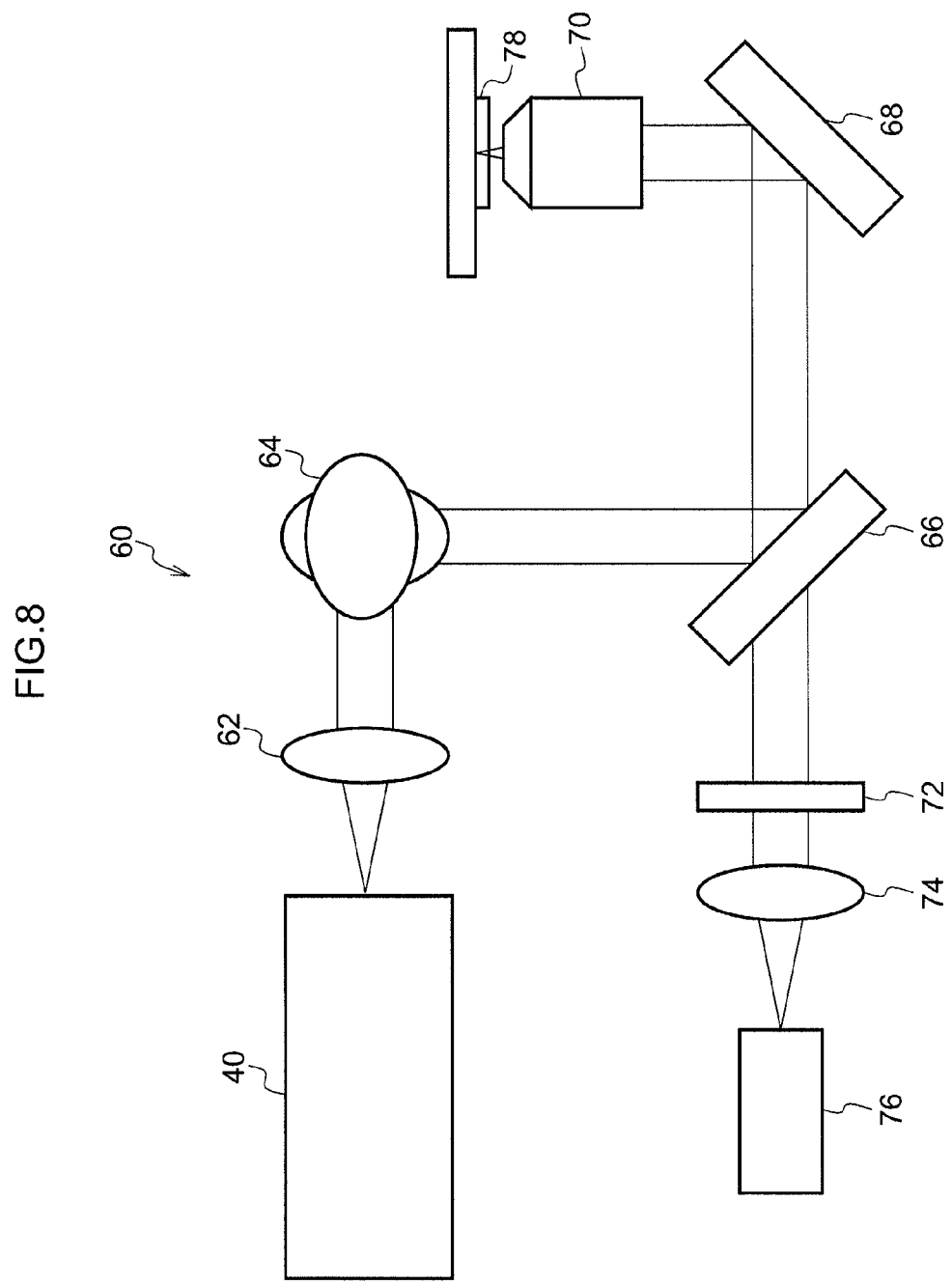
FIG. 8 is a schematic structural diagram of a non-linear optical microscopy device relating to a third exemplary embodiment.

In FIG. 8, schematic structure of a non-linear optical microscopy device 60 relating to the present exemplary embodiment is illustrated. As shown in FIG. 8, the nonlinear optical microscopy device 60 is structured to include the mode-locked laser device 40, a collimator lens 62, a galvano mirror 64, a dichroic mirror 66, an Au mirror 68, an objective lens 70, a filter 72, a focusing lens 74 and a PMT (photomultiplier tube) 76.

Pulse light of, for example, 1045 nm that is emitted from the mode-locked laser device 40 is collimated by the collimator lens 62 and reflected in the direction of the dichroic mirror 66 by the galvano mirror 64.

The dichroic mirror 66 functions to reflect near-infrared light and transmit visible light. The pulse light from the galvano mirror 64 is reflected in the direction of the Au mirror 68 by the dichroic mirror 66.

The Au mirror 68 reflects the pulse light from the dichroic mirror 66 in the direction of the objective lens 70, which has, for example, an NA of 0.75.

The objective lens 70 focuses incident light on a sample 78. Fluorescence from the sample 78 passes through the objective lens 70 and is reflected by the Au mirror 68 in the direction of the dichroic mirror 66. Then, the fluorescence that has passed through the dichroic mirror 66 passes through the filter 72, which cuts near-infrared light, and is focused at the PMT 76 by the focusing lens 74 and detected.

Figure 9:
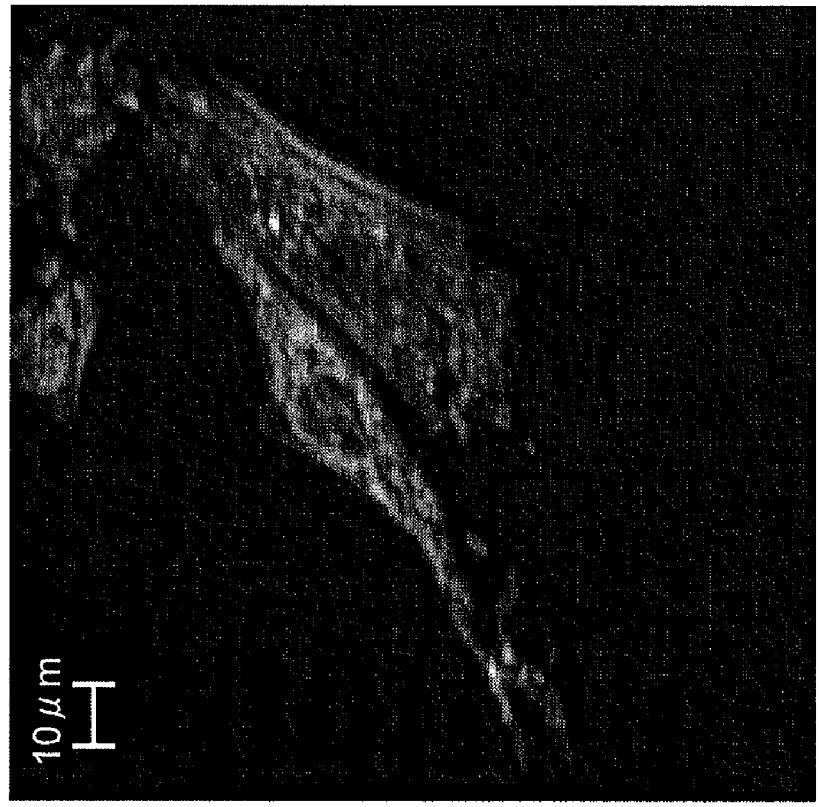
FIG. 9 is a view showing an image of a sample acquired by the non-linear optical microscopy device.

The nonlinear optical microscopy device 60 with this structure, while scanning the galvano mirror 64 in a predetermined direction, detects intensities of fluorescence caused by secondary photon absorption at respective points of the sample 78, and thus may acquire an image. In FIG. 9, an image acquired by the nonlinear optical microscopy device 60 is shown, the sample being a skin fibroblast from a muntjac deer that has been dyed with a fluorescent pigment with an absorption peak in the green wavelength region (FluoCells prepared slide #6:F36925). As illustrated in FIG. 9, although a fluorescent dyed sample is used as the sample and fluorescence due to secondary photon absorption is detected, even with non-fluorescent dyed samples, of collagen or the like, SH (second harmonic) light from the collagen may be detected and imaged.

By using the inexpensive, small-size mode-locked laser device 40 described in the second exemplary embodiment, as in the nonlinear optical microscopy device 60 relating to the present exemplary embodiment, an inexpensive, small-size non-linear optical microscopy device capable of acquiring secondary photon or SHG (second harmonic generation) microscopic images may be realized. Moreover, with non-linear optical microscopy devices that use titanium-sapphire mode-locked lasers for light sources, because the sizes of the light sources are large, assembly for use on laboratory tables is usual. However, by using the small mode-locked laser device 40 as the light source in the nonlinear optical microscopy device 60 relating to the present exemplary embodiment, a portable non-linear optical microscopy device may be realized.

Fourth Exemplary Embodiment

Next, a fourth exemplary embodiment of the present invention will be described. In the present exemplary embodiment, an ultrashort pulse light source device that uses the mode-locked laser device 40 described in the second exemplary embodiment will be described.

Figure 10:
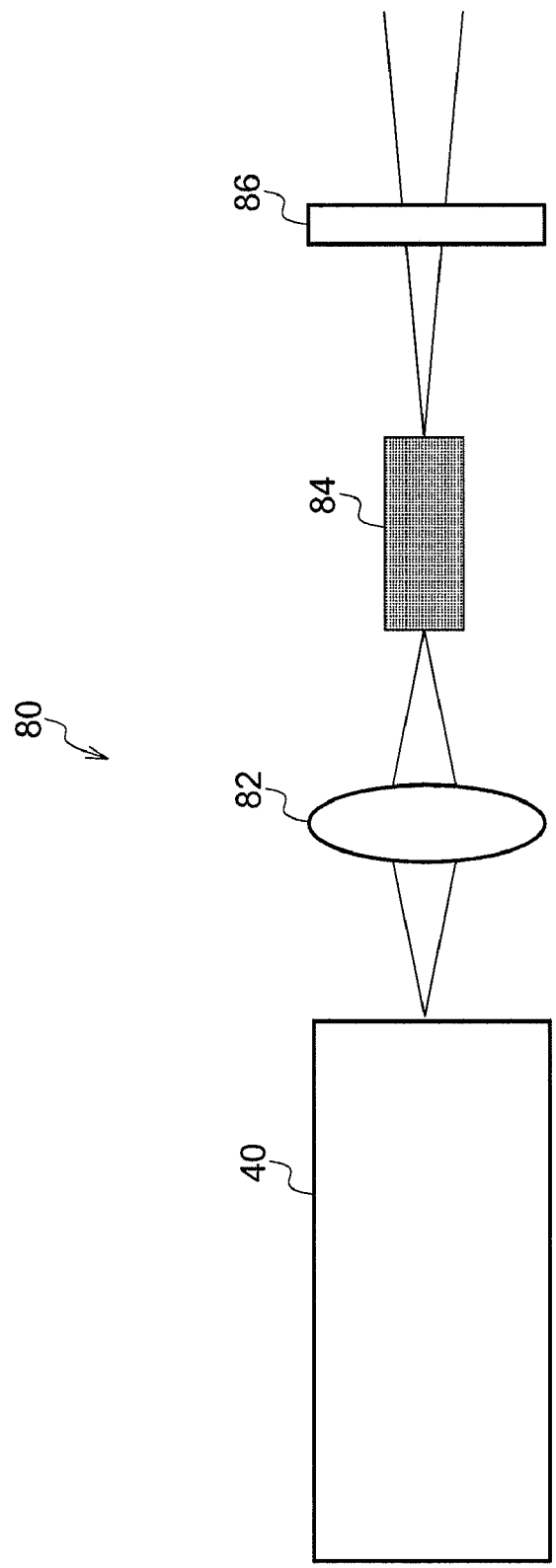
FIG. 10 is a schematic structural diagram of an ultrashort pulse light source device relating to a fourth exemplary embodiment.

In FIG. 10, an ultrashort pulse light source device 80 relating to the present exemplary embodiment is illustrated. As shown in FIG. 10, the ultrashort pulse light source device 80 is structured to include the mode-locked laser device 40 described in the second exemplary embodiment, a focusing lens 82, a PPKTP (periodically poled KTiOPO$_4$) 84 to serve as a non-linear crystal, and a filter 86.

The pulse light emitted from the mode-locked laser device 40 is focused at the PPKTP with, for example, a length of 4.8 mm by the focusing lens 82 with, for example, a focusing length of 6 mm. As a result, light of a half-wavelength (for example, 522 nm) is generated by the PPKTP 84. This light passes through the filter 86, which cuts near-infrared light, and thus green ultrashort pulse light is provided.

Here, an inversion domain period of the PPKTP 84 is, for example, a period matching the basic wavelength of 1045 nm.

Figure 11:
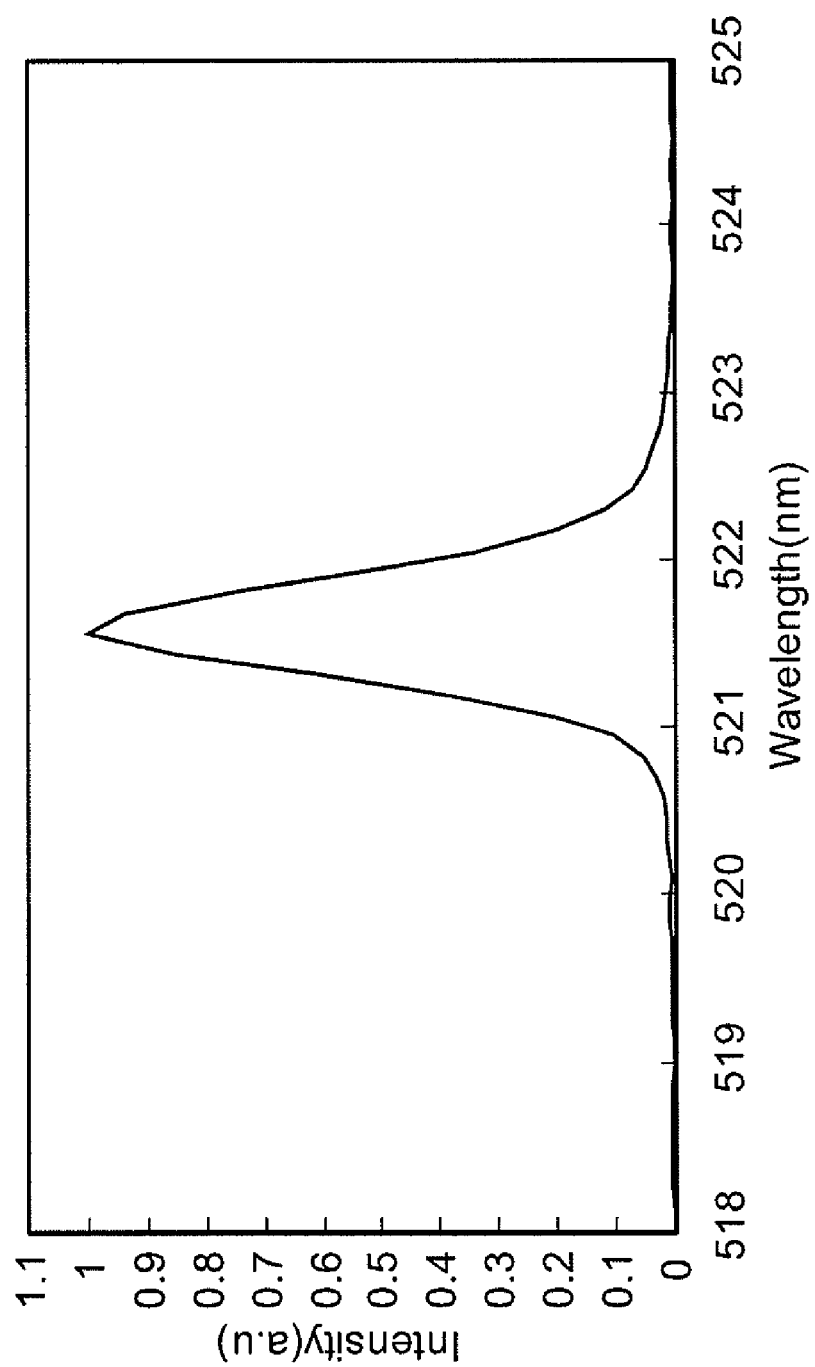
FIG. 11 is a waveform diagram showing a waveform of an ultrashort optical pulse.
Figure 12:
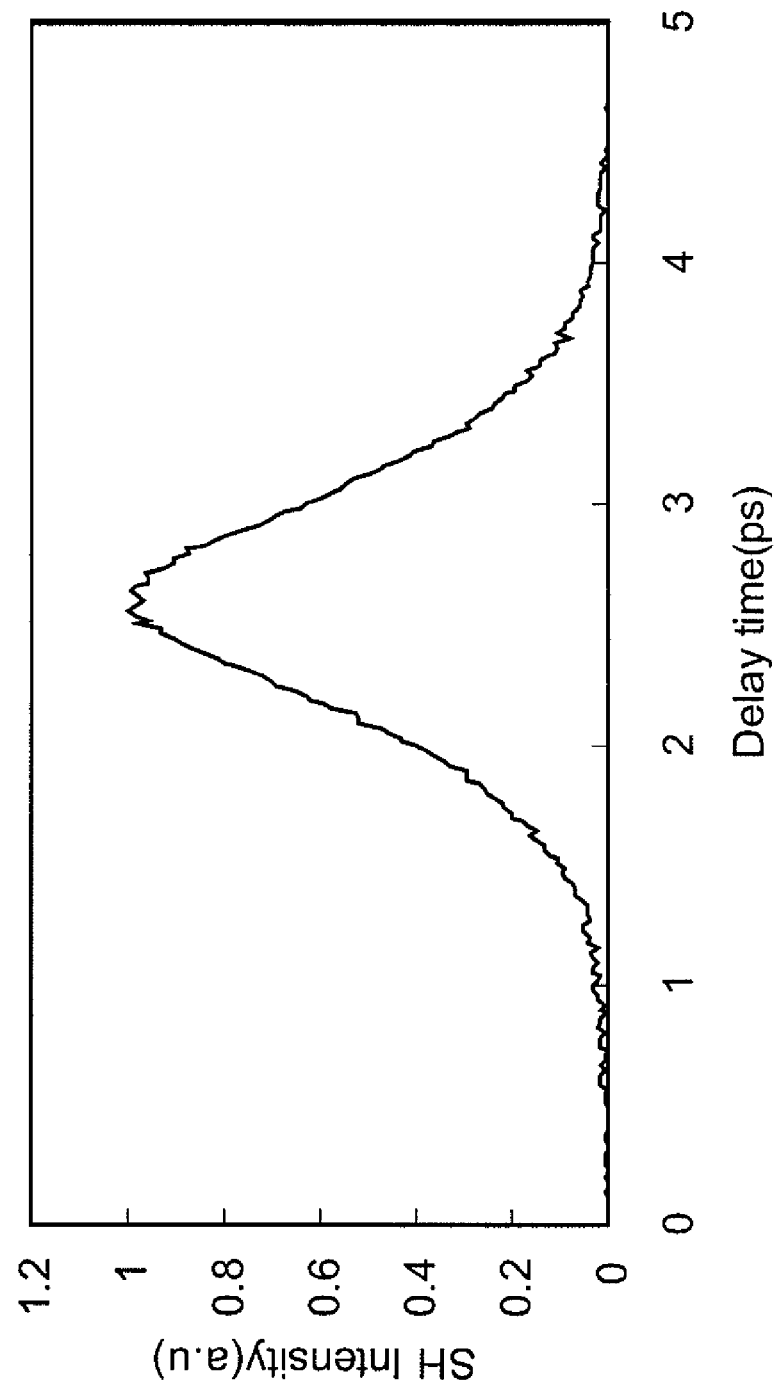
FIG. 12 is a waveform diagram showing a waveform of an ultrashort optical pulse.

With the ultrashort pulse light source device 80 of this structure, green ultrashort pulses with average output power 50 mW, pulse width 700 fs and wavelength 522 nm may be provided. In FIG. 11 and FIG. 12, waveforms of the green ultrashort pulses emitted from the ultrashort pulse light source device 80 are illustrated.

In the present exemplary embodiment, a case of using the mode-locked laser device 40 that employs a solid-state laser medium doped with Yb as the basic wavelength light source has been described. However, using mode-locked laser devices that employ Cr-doped solid-state laser mediums and various non-linear crystals, ultrashort pulse lights with wavelengths in the visible wavelength region of 350 to 700 nm may be obtained.

Fifth Exemplary Embodiment

Next, a fifth exemplary embodiment of the present invention will be described. In the present exemplary embodiment, a recording device that uses the ultrashort pulse light source device 80 described in the fourth exemplary embodiment will be described.

Figure 13:
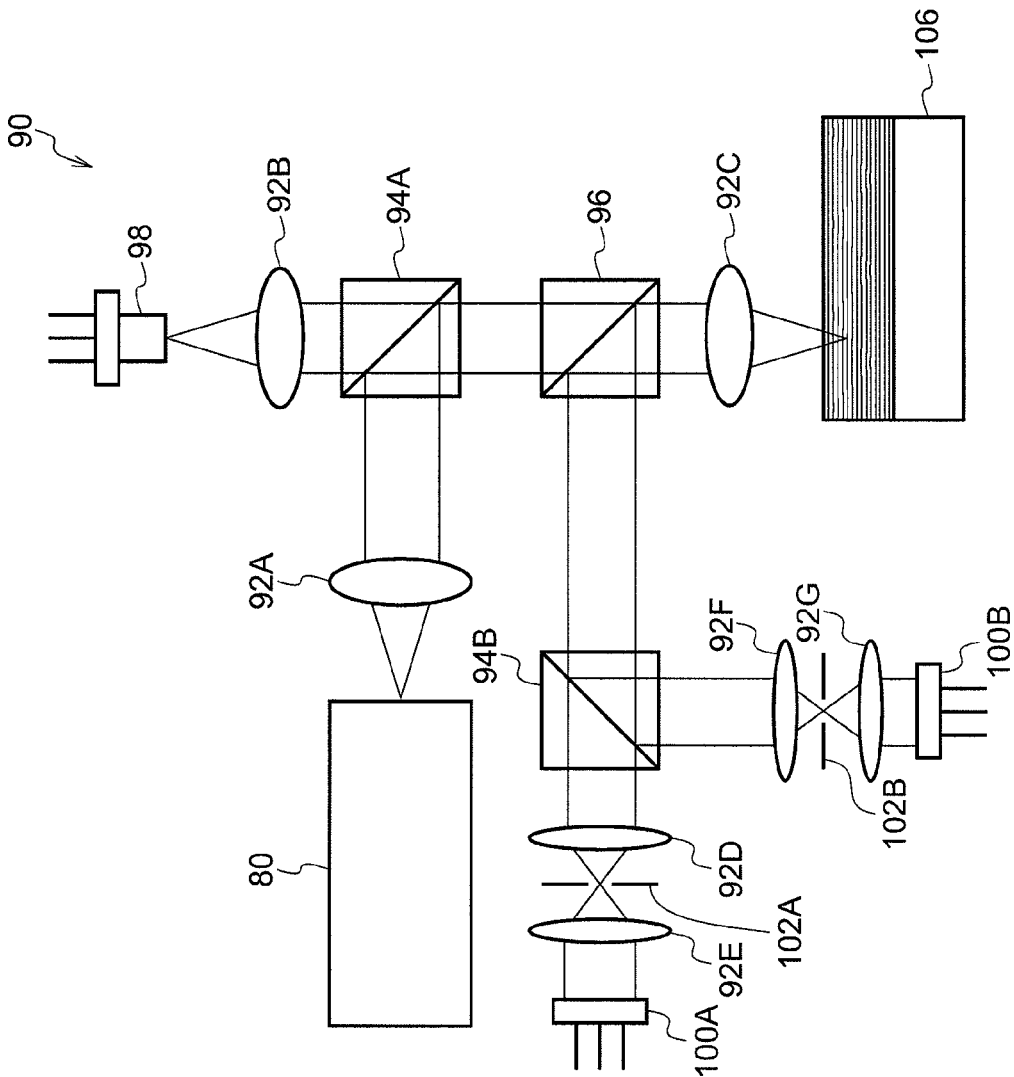
FIG. 13 is a schematic structural diagram of a recording device relating to a fifth exemplary embodiment.

In FIG. 13, schematic structure of a recording device 90 relating to the present exemplary embodiment is illustrated. As shown in FIG. 13, the recording device 90 is structured to include the ultrashort pulse light source device 80 described in the fourth exemplary embodiment that emits light with a wavelength in the visible region, lenses 92A to 92G, dichroic beam splitters 94A and 94B, a half-beam splitter 96, a reading light source 98, photodiodes 100A and 100B, and pinholes 102A and 102B. The recording device 90 writes information to an optical disc 106 and reads information that has been recorded at the optical disc 106.

The pulse light emitted from the ultrashort pulse light source device 80 is used for writing of the optical disc 106. The writing pulse light emitted from the ultrashort pulse light source device 80 passes through the lens 92A, is reflected in the direction of the half-beam splitter 96 by the dichroic beam splitter 94A, passes through the half-beam splitter 96, and is focused on the optical disc 106 by the lens 92C.

The optical disc 106 is movable in the focusing direction of the pulse light by an illustrated driving section, and the focusing position may be altered in the focusing direction.

Returning light of the writing pulse light focused on the optical disc 106 is reflected in the direction of the dichroic beam splitter 94B by the half-beam splitter 96, passes through the dichroic beam splitter 94B, then passes through a confocal optical system formed of the lenses 92D and 92E and the pinhole 102A, and is detected by the photodiode 100A.

The photodiode 100A converts the detected light to voltages and outputs the voltages to an unillustrated control section. The control section, while monitoring the detected voltages from the photodiode 100A, corrects the focusing position of the writing pulse light on the optical disc 106.

For the reading light source 98, a semiconductor laser that outputs laser light with, for example, a wavelength of 405 nm may be used. However, the ultrashort pulse light source device 80 described in the fourth exemplary embodiment may also be used, outputting light with a wavelength different from the writing pulse light.

The pulse light emitted from the reading light source 98 passes through the lens 92B, the dichroic beam splitter 94A, the half-beam splitter 96 and the lens 92C, and is hence focused on the optical disc 106. Returning light of the reading pulse light focused on the optical disc 106, or fluorescence excited by the reading pulse light, passes through the lens 92C, is then reflected in the direction of the dichroic beam splitter 94B by the half-beam splitter 96, passes through a confocal optical system formed of the lenses 92F and 92G and the pinhole 102B, and is detected by the photodiode 100B.

In the present exemplary embodiment, fluorescence may be detected for reading, and intensity variations of reading light that are caused by refractive index variations may be detected.

Thus, by using the ultrashort pulse light source device 80 described in the fourth exemplary embodiment, a low-cost recording device that may be applied to a desktop-size personal computer may be realized. Further, in the mode-locked laser device 40 described in the second exemplary embodiment that is used in the ultrashort pulse light source device 80 described in the fourth exemplary embodiment, because the repetition frequency is high, at 2.85 GHz, writing with a high transfer rate is possible.

Sixth Exemplary Embodiment

Next, a sixth exemplary embodiment of the present invention will be described. In the present exemplary embodiment, a broad bandwidth light source device that uses the mode-locked laser device 40 described in the second exemplary embodiment will be described.

Figure 14:
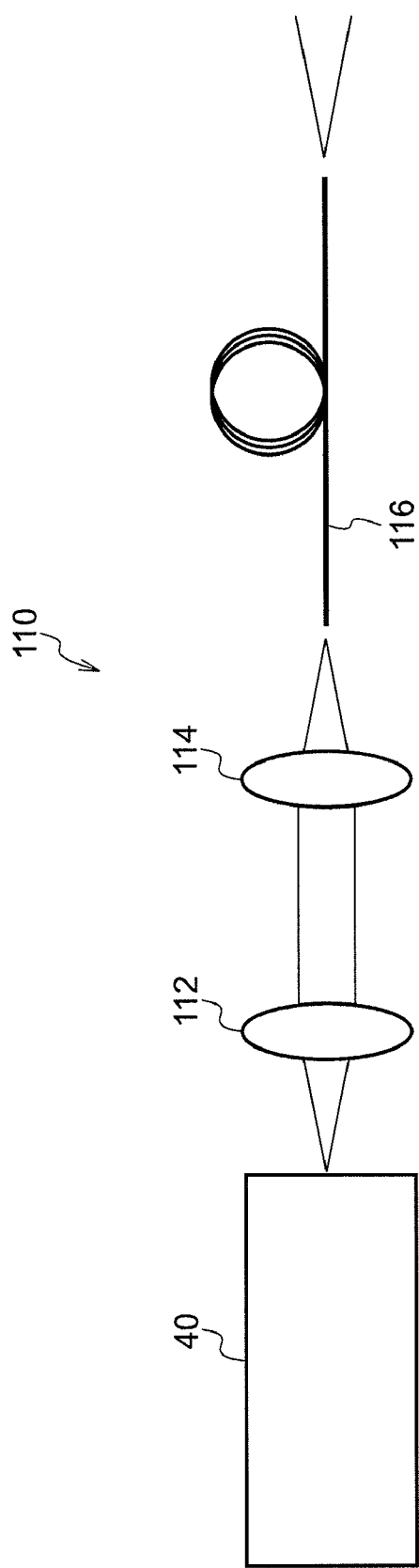
FIG. 14 is a schematic structural diagram of a broad bandwidth light source device relating to a sixth exemplary embodiment.

In FIG. 14, schematic structure of a broad bandwidth light source device 110 relating to the present exemplary embodiment is illustrated. As shown in FIG. 14, the broad bandwidth light source device 110 is structured to include the mode-locked laser device 40 described in the second exemplary embodiment, a collimator lens 112, a focusing lens 114 and a non-linear optical fiber 116.

The mode-locked laser device 40 emits pulse light with, for example, a pulse width of 210 fs and an average output power of 600 mW. This pulse light is collimated by the collimator lens 112 with, for example, a focusing length f of 100 mm, and is focused by the focusing lens 114 with, for example, a focusing length f of 6.2 mm on a non-linear fiber manufactured by, for example, CRYSTAL FIBRE A/S (SC-5.0-1040).

Figure 15:
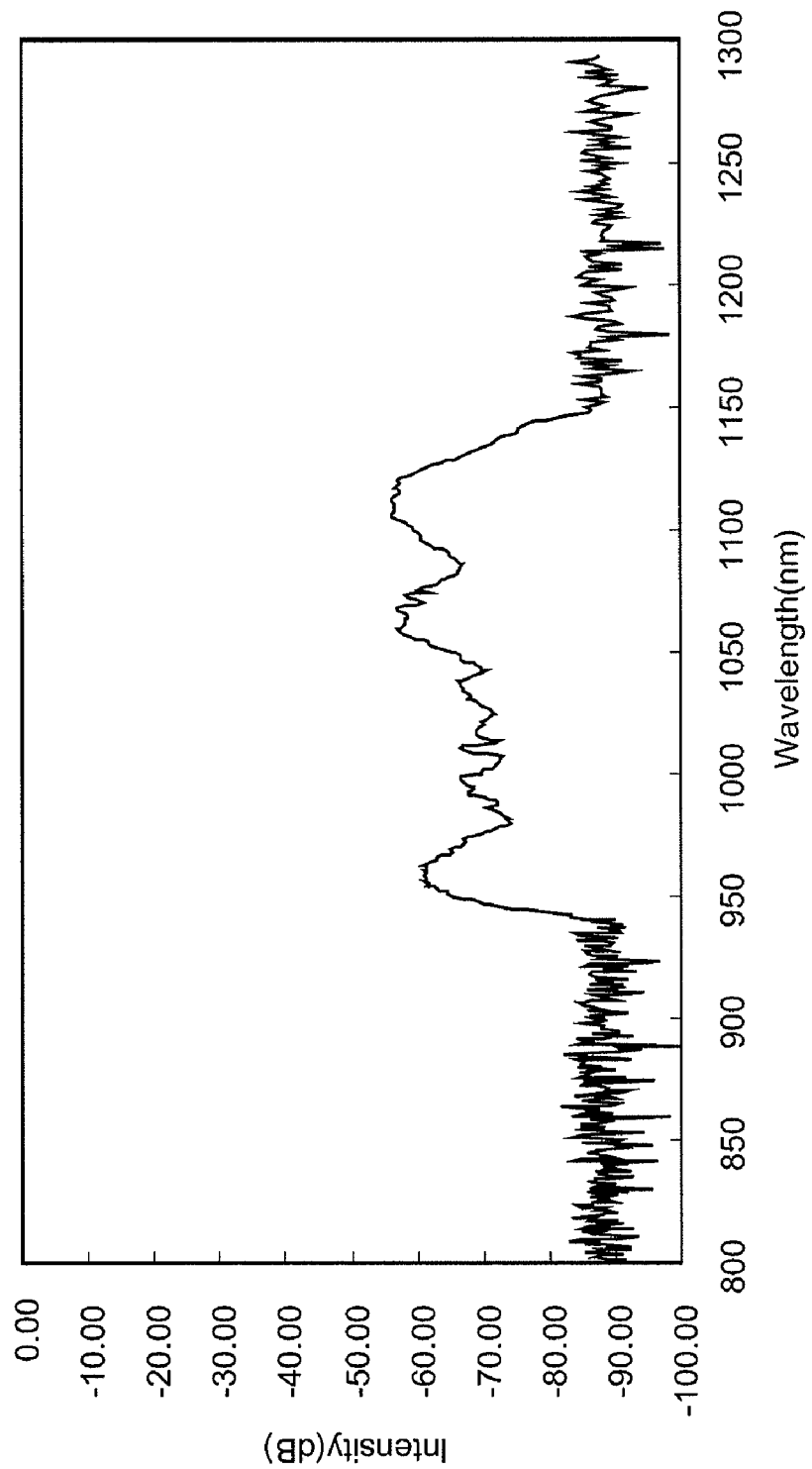
FIG. 15 is a waveform diagram of broad bandwidth light outputted by the broad bandwidth light source device.

High output broad bandwidth light with, for example, an average output power of 200 mW and a wavelength bandwidth of 200 nm as illustrated in FIG. 15 is provided by the broad bandwidth light source device 110 with this structure. Thus, by using the small, low-cost mode-locked laser device 40, a small, low-cost broad bandwidth light source device is obtained.

Seventh Exemplary Embodiment

Next, a seventh exemplary embodiment of the present invention will be described. In the present exemplary embodiment, an optical coherence tomography device that uses the broad bandwidth light source device 110 described in the sixth exemplary embodiment will be described.

Figure 16:
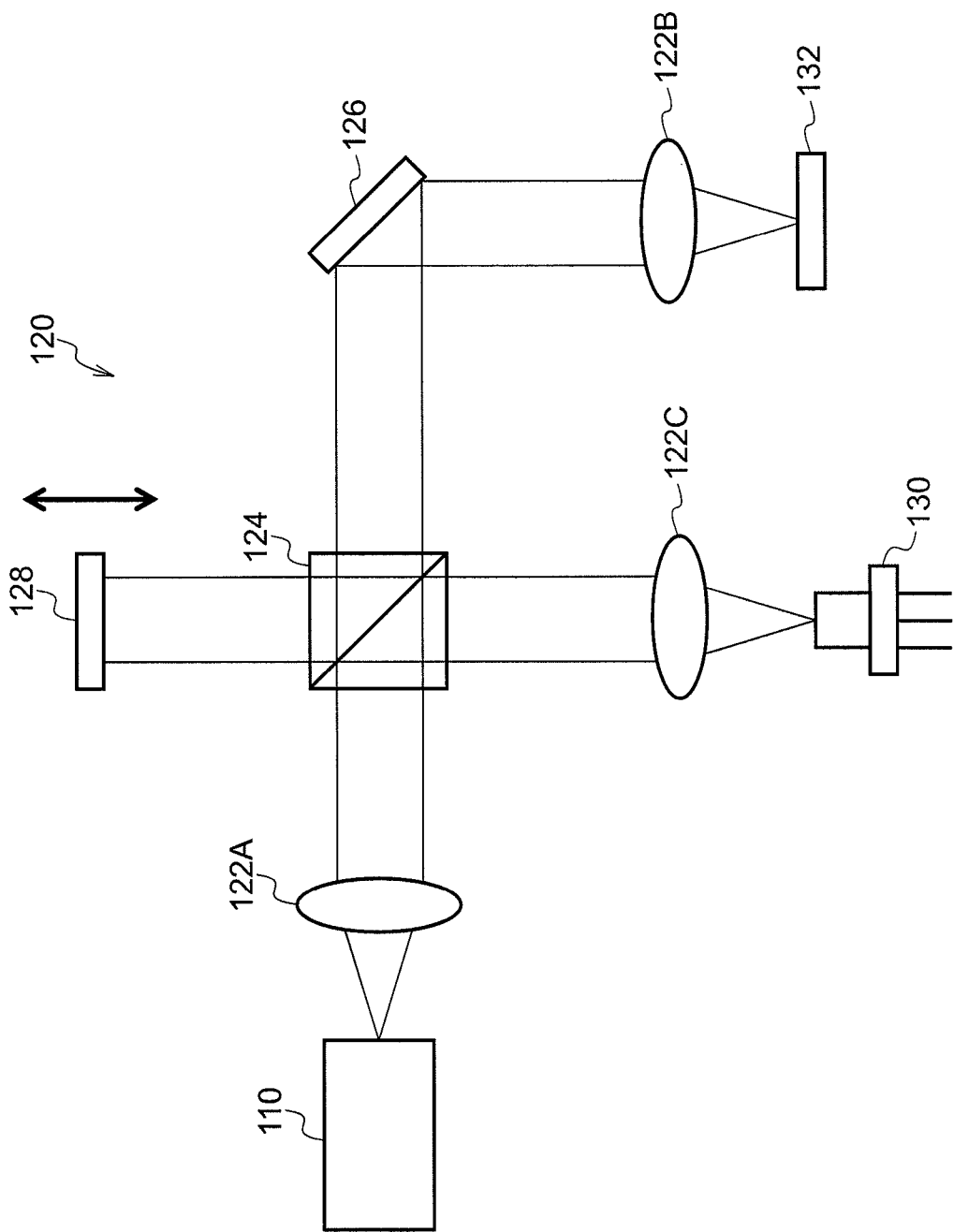
FIG. 16 is a schematic structural diagram of an optical coherence tomography device relating to a seventh exemplary embodiment.

In FIG. 16, schematic structure of an optical coherence tomography (OCT) device 120 relating to the present exemplary embodiment is illustrated. As shown in FIG. 16, the optical coherence tomography device 120 is structured to include the broad bandwidth light source device 110 described in the sixth exemplary embodiment, lenses 122A to 122C, a half-beam splitter 124, a galvano mirror 126, a broad bandwidth reflection mirror 128 and a photodiode 130.

The broad bandwidth light emitted from the broad bandwidth light source device 110 is correlated by the lens 122A, after which a portion of the light is reflected toward the broad bandwidth reflection mirror 128 by the half-beam splitter 124 and the rest is transmitted toward the galvano mirror 126.

The light transmitted toward the galvano mirror 126 is reflected toward the lens 122B by the galvano mirror 126, and is focused onto a sample 132 by the lens 122B.

Returning light from the sample 132 and reflected light from the broad bandwidth reflection mirror 128 are combined and interfered at the half-beam splitter 124, and a portion of this light is focused onto the photodiode 130 by the lens 122C and detected.

The galvano mirror 126 scans in planar directions of the sample 132, and the sample 132 is moved in the focusing direction of the broad bandwidth light and, simultaneously, the broad bandwidth reflection mirror 128 is moved in the direction of illumination of the broad bandwidth light (the direction of the arrow in the drawing). Degrees of interference of the lights combined by the half-beam splitter 124 are detected. Thus, a three-dimensional image of the sample 132 may be acquired.

Thus, by using the small-size broad bandwidth light source device 110 described in the sixth exemplary embodiment, a small-size, low-cost, ultrahigh-resolution optical coherence tomography device may be constituted. This small optical coherence tomography device with high portability may be used for, for example, pathological diagnosis in surgery locations and the like, and may even be used in the home.

What is claimed is:

1. A mode-locked laser device comprising:
a resonator;
a solid-state laser medium that is disposed in the resonator and outputs oscillation light in accordance with the incidence of excitation light;
a saturable absorber that is disposed in the resonator and induces soliton mode-locking;
a group velocity dispersion correction component that is disposed in the resonator and controls group velocity dispersion in the resonator; and
an excitation portion that causes excitation light to be incident at the solid-state laser medium,
wherein a resonator length of the resonator is at least a resonator length with which soliton mode-locking is inducible and is less than a resonator length with which non-soliton mode-locking is inducible;
wherein the resonator length satisfies the following equation (1):

$$\frac{c \times E_{c,p,s} \times T}{2 \times P_{out}} \leq L < \frac{c \times E_{c,p} \times T}{2 \times P_{out}} \quad (1)$$

in which L is the resonator length, c is the speed of light, $E_{c,p,s}$ is a mode-locking threshold energy of soliton mode-locking, which is expressed in the following equation (2), T is transmissivity of an optical member at a side at which the oscillation light is outputted, Pout is a desired average output power of the oscillation light outputted from the solid-state laser medium, and $E_{c,p}$ is a mode-locking threshold energy of non-soliton mode-locking, which is expressed in the following equation (3):

$$E_{c,p,s} = \frac{1}{3E_{sat,L}gK^2} + \frac{2^{1/3}}{3E_{sat,L}gK^2\left(-2 + 27E_{sat,L}^2g^2K^4E_{c,p}^2 + \sqrt{-4 + (-2 + 27E_{sat,L}^2g^2K^4E_{c,p}^2)^2}\right)^{1/3}} +$$

$$\frac{\left(-2 + 27E_{sat,L}^2g^2K^4E_{c,p}^2 + \sqrt{-4 + (-2 + 27E_{sat,L}^2g^2K^4E_{c,p}^2)^2}\right)^{1/3}}{3 \times 2^{1/3}E_{sat,L}gK^2}$$

K being expressed by the following equation $$K = \frac{4\pi n_2 L_K}{D_2 A_L \lambda_o \Delta v_g} \cdot \frac{0.315}{1.76} \quad (3)$$

$$E_{c,p} = \sqrt{F_{sat,L} \times F_{sat,s} \times A_L \times A_S \times \Delta R}$$

in which $E_{sat,L}$ is expressed by $F_{sat,L}*A_L$, $F_{sat,L}$ is a saturation fluence of the solid-state laser medium, and $A_L$ is a beam diameter of the oscillation light in the solid-state laser medium,
and g is a gain of the solid-state laser medium, $n_2$ is a non-linear refractive index of the solid-state laser medium, $L_K$ is a length of the solid-state laser medium, $D_2$ is a negative dispersion amount in the resonator $\lambda_o$ is a central wavelength of the oscillation light, $\Delta v_g$ is a bandwidth of the oscillation light, $F_{sat,S}$ is a saturation fluence of the saturable absorber, $A_S$ is a beam diameter of the oscillation light in the saturable absorber, and $\Delta R$ is a modulation depth of the saturable absorber.

2. The mode-locked laser device according to claim 1, wherein the resonator length is at most 150 mm.

3. The mode-locked laser device according to claim 2, wherein the resonator length is at most 75 mm.

4. The mode-locked laser device according to claim 1, wherein a stimulated emission cross section of the solid-state laser medium is at least $1 \times 10^{-21}$ cm$^2$ and at most $5 \times 10^{-19}$ cm$^2$.

5. The mode-locked laser device according to claim 4, wherein the solid-state laser medium comprises any of Yb:KGW (KGd(WO$_4$)$_2$), Yb:KYW (KY(WO$_4$)$_2$), Yb:YAG (Y$_3$Al$_5$O$_{12}$), Yb:Y$_2$O$_3$, Yb:Sc$_2$O$_3$, Yb:Lu$_2$O$_3$, Yb:GdCOB (Ca$_4$GdO(BO$_3$)$_3$), Yb:SYS (SrY$_4$(SiO$_4$)$_3$), Yb:BOYS (Sr$_3$Y(BO$_3$)$_3$), Yb:YVO$_4$, Yb:GdVO$_4$, Alexandrite (Cr:BeAl$_2$O$_4$), Cr:LiSAF (LiSrAlF$_6$), Cr:LiSGAF (LiSrGaF$_6$), Cr:LiCAF (LiCaAlF$_6$)), Cr:forsterite (Mg$_2$SiO$_4$), Cr:YAG (Y$_3$Al$_5$O$_{12}$), Cr:Ca$_2$GeO$_4$, Ti:Al$_2$O$_3$, Nd:Glass and Er:Yb:Glass.

6. The mode-locked laser device according to claim 1, wherein a negative dispersion amount in the resonator is at least −3000 fs$^2$ and at most 0 fs$^2$.

7. The mode-locked laser device according to claim 6, wherein the negative dispersion amount in the resonator is at least −1000 fs$^2$ and at most 0 fs$^2$.

8. The mode-locked laser device according to claim 1, wherein the transmissivity of the optical member at the side at which the oscillation light is outputted is at least 0.1% and at most 5%.

9. The mode-locked laser device according to claim 8, wherein the transmissivity is at least 0.1% and at most 3%.

10. The mode-locked laser device according to claim 1, wherein the modulation depth of the saturable absorber is at least 0.5% and at most 5%, and the saturation fluence of the saturable absorber is at least 50 μJ/cm$^2$ and at most 200 μJ/cm$^2$.

11. The mode-locked laser device according to claim 1, wherein the average output power is at least 0.1 mW and at most 10 W.

12. The mode-locked laser device according to claim 11, wherein the average output power is at least 0.1 mW and at most 5 W.

13. The mode-locked laser device according to claim 1, wherein the resonator is formed with a pair of resonator mirrors disposed on a straight line.

14. The mode-locked laser device according to claim 1, wherein the saturable absorber is a semiconductor saturable absorber mirror.

15. A non-linear optical microscopy device comprising:
a mode-locked laser device according to claim 1;
a first focusing optical system that focuses pulse light from the mode-locked laser device at a sample;
a second focusing optical system that focuses fluorescence from the sample; and
a detection section that detects the fluorescence focused by the second focusing optical system.

16. An ultrashort pulse light source device comprising:
a mode-locked laser device according to claim 1;
a non-linear crystal;
a focusing lens that focuses pulse light from the mode-locked laser device at the non-linear crystal; and
a filter that, of light transmitted through the non-linear crystal, cuts near-infrared light and transmits ultrashort pulse light in the visible wavelength region.

17. A recording device comprising:

an ultrashort pulse light source device according to claim 16; and a focusing optical system that focuses ultrashort pulse light from the ultrashort pulse light source device at a recording medium to serve as writing light.

18. A broad bandwidth light source device comprising:

a mode-locked laser device according to claim 1;

a non-linear optical fiber; and a focusing lens that focuses pulse light from the mode-locked laser device at the non-linear fiber.

19. An optical coherence tomography device comprising:

a broad bandwidth light source device according to claim 18;

a reflection portion that reflects light from the broad bandwidth light source device in a predetermined direction;

a focusing optical system that focuses other light from the broad bandwidth light source device at a sample;

a movement section that relatively moves the light focused by the focusing optical system and the sample; and a detection section that detects interference light between the light reflected by the reflection portion and light returned from the sample.

* * * * *